US008017400B2

(12) United States Patent
Toriyama et al.

(10) Patent No.: US 8,017,400 B2
(45) Date of Patent: Sep. 13, 2011

(54) METHOD FOR TRANSFORMATION USING MUTANT ACETOLACTATE SYNTHASE GENE

(75) Inventors: Kinya Toriyama, Miyagi (JP); Ayako Okuzaki, Miyagi (JP); Koichiro Kaku, Tokyo (JP); Kiyoshi Kawai, Tokyo (JP); Tsutomu Shimizu, Tokyo (JP)

(73) Assignees: Kumiai Chemical Industry Co., Ltd., Tokyo (JP); Tohoku University, Sendai-Shi, Miyagi (JP)

( * ) Notice: Subject to any disclaimer, the term of this patent is extended or adjusted under 35 U.S.C. 154(b) by 684 days.

(21) Appl. No.: 11/920,161

(22) PCT Filed: May 9, 2006

(86) PCT No.: PCT/JP2006/309622
§ 371 (c)(1),
(2), (4) Date: Nov. 9, 2007

(87) PCT Pub. No.: WO2006/121178
PCT Pub. Date: Nov. 16, 2006

(65) Prior Publication Data
US 2009/0217420 A1    Aug. 27, 2009

(30) Foreign Application Priority Data
May 9, 2005   (JP) .................................. 2005-136186

(51) Int. Cl.
*C12N 15/82* (2006.01)
(52) U.S. Cl. ........................................ 435/468; 800/300
(58) Field of Classification Search .................. None
See application file for complete search history.

(56) References Cited

U.S. PATENT DOCUMENTS

| 5,013,659 A * | 5/1991 | Bedbrook et al. ........... 536/23.2 |
| 5,633,437 A | 5/1997 | Bernasconi et al. |
| 2004/0088753 A1 * | 5/2004 | Shimizu et al. ............... 800/278 |
| 2005/0283855 A1 | 12/2005 | Kaku et al. |

FOREIGN PATENT DOCUMENTS

| JP | 63-71184 A | 3/1988 |
| JP | 4-311392 A | 11/1992 |
| JP | 5-227964 A | 9/1993 |
| JP | 11-504213 A | 4/1999 |
| WO | WO-96/33270 A1 | 10/1996 |
| WO | WO-97/08327 A1 | 3/1997 |
| WO | WO-00/27182 A1 | 5/2000 |
| WO | WO-01/85970 A2 | 11/2001 |
| WO | WO-02/44385 A1 | 6/2002 |
| WO | WO-03/083118 A1 | 10/2003 |
| WO | WO-2005/020673 A1 | 3/2005 |

OTHER PUBLICATIONS

Pang et al., Biochemistry, vol. 38, No. 16, pp. 5222-5231, 1999.
Hershey et al., Plant Molecular Biology, vol. 40, pp. 795-806, 1999.
Lee et al., The EMBO Journal, vol. 7, No. 5, pp. 1241-1248, 1988.
Burr et al., Trendsin Genetics, vol. 7, No. 2, pp. 55-61, 1991.
Fang et al., Plant Molecular Biology, vol. 18, pp. 1185-1187, 1992.
Thomas Ray, Plant Physiology, vol. 75, pp. 827-831, 1984.
Shaner et al., Plant Physiology, vol. 76, pp. 545-546, 1984.
Subramanian et al., Plant Physiology, vol. 96, pp. 310-313, 1991.
Shimizu et al., Journal of Pesticide Science, vol. 19, pp. 59-67, 1994.
Mourad et al., Planta, vol. 188, pp. 491-497, 1992.
Guttieri et al., Weed Science, vol. 43, pp. 175-178, 1995.
Bemasconi et al., The Journal of Biological Chemistry, vol. 270, No. 29, pp. 17381-17385, 1995.
Lee et al., FEBS Letter, vol. 452, pp. 341-345, 1999.
Hattori et al., Mol. Gen. Genet., vol. 246, pp. 419-425, 1995.
Alison et al., Plant Physiology, vol. 111, pp. 1353-1354, 1996.
Rajasekaran et al., Plant Science, vol. 119, pp. 115-124, 1996.
Mourad et al., Mol. Gen. Genet., vol. 243, pp. 178-184, 1994.
Ott et al., J. Mol. Biol., vol. 263, pp. 359-368, 1996.
Okuzaki et al., Chimeric RNA/DNA oligonucleotide-directed gene targeting in rice, Plant Cell Reports, vol. 22, No. 7, pp. 509-512, 2004, XP002493782.
Osakabe et al., The mutant form of acetolactate synthase genomic DNA from rice is an efficient selectable marker for genetic transformation, Molecular Breeding, vol. 16, No. 4, pp. 313-320, 2005, XP019258765.
Okuzaki et al., A novel mutated acetolactate synthase gene conferring specific resistance to pyrimidinyl carboxy herbicides in rice, Plant Molecular Biology, vol. 64, No. 1-2, pp. 219-224, 2007, XP019507416.
Kawai et al., A novel mutant acetolactate synthase gene from rice cells, which confers resistance to ALS-inhibiting herbicides, Journal of Pesticide Science, vol. 32, No. 2, pp. 89-98, 2007, XP002493783.
Kawai et al., Functional analysis of transgenic rice plants expressing a novel mutated ALS gene of rice, Journal of Pesticide Science, vol. 32, No. 4, pp. 385-392, 2007, XP002493784.
Shimizu, T. et al., Molecular Characterization of Acetolactate Synthase in Resistant Weeds and Crops., ACS Symposium Series, 2005, pp. 255 to 271.
Mazur B.J. and Falco S.C., The Development of Herbicide Resistant Crops., Annual Review of Plant Physiology and Plant Molecular Biology, 1989, vol. 40, pp. 441 to 470.
Pang S.S. et al., Crystal Structure of Yeast Acetohydroxyacid Synthase: A Target for Herbicidal Inhibitors., J. Mol. Biol., 2002, vol. 317, pp. 249 to 262.

(Continued)

*Primary Examiner* — David H Kruse
(74) *Attorney, Agent, or Firm* — Birch, Stewart, Kolasch & Birch, LLP

(57) ABSTRACT

Transformed cells are efficiently selected using a mutant ALS gene having high specificity to PC herbicides. The transformation method comprises the steps of: transforming a host cell with a recombination vector containing a gene of interest and a gene coding for a mutant acetolactate synthase having mutation of glycine corresponds to position 95 of the amino acid sequence of a wild-type acetolactate synthase derived from rice to alanine; culturing the transformed cell obtained in the former step in the presence of a pyrimidinyl carboxy herbicide; and wherein the gene coding for the mutant acetolactate synthase is used as a selection marker.

6 Claims, 7 Drawing Sheets
(1 of 7 Drawing Sheet(s) Filed in Color)

OTHER PUBLICATIONS

Chipman D. et al., Biosynthesis of 2-aceto-2-hydroxy acids: acetolactate synthases and acetohydroxyacid synthases., Biochim. Biophys. Acta, 1998, vol. 1385, pp. 401 to 419.

Tan S. et al., Imidazolinone-tolerant crops: history, current status and future., Pest Manag. Sci., 2005.1, vol. 61, No. 3, pp. 246 to 257.

* cited by examiner

Fig. 1

| | | |
|---|---|---|
| wild type ALS | 1 MATTAAAAAALSAAATAKTGRKNHQRHHVLPARGRVGAAAVRCSAVSPVTPPSPAPPAT | 60 |
| G95A ALS | 1 ............................................................ | 60 |
| | ************************************************************ | |
| wild type ALS | 61 PLRPWGPAEPRKGADILVEALERCGVSDVFAYPGGASMEIHQALTRSPVITNHLFRHEQG | 120 |
| G95A ALS | 61 ..........................A................................. | 120 |
| | ************************** ********************************* | |
| wild type ALS | 121 EAFAASGYARASGRVGVCVATSGPGATNLVSALADALLDSVPMVAITGQVPRRMIGTDAF | 180 |
| G95A ALS | 121 ............................................................ | 180 |
| | ************************************************************ | |
| wild type ALS | 181 QETPIVEVTRSITKHNYLVLDVEDIPRVIQEAFFLASSGRPGPVLVDIPKDIQQQMAVPV | 240 |
| G95A ALS | 181 ............................................................ | 240 |
| | ************************************************************ | |
| wild type ALS | 241 WDTSMNLPGYIARLPKPPATELLEQVLRLVGESRRPILYVGGGCSASGDELRWFVELTGI | 300 |
| G95A ALS | 241 ............................................................ | 300 |
| | ************************************************************ | |
| wild type ALS | 301 PVTTTLMGLGNFPSDDPLSLRMLGMHGTVYANYAVDKADLLLAFGVRFDDRVTGKIEAFA | 360 |
| G95A ALS | 301 ............................................................ | 360 |
| | ************************************************************ | |
| wild type ALS | 361 SRAKIVHIDIDPAEIGKVKQPHVSTCADVKLALQGLNAILQQSTTKTSSDFSAWHNELDQ | 420 |
| G95A ALS | 361 ............................................................ | 420 |
| | ************************************************************ | |
| wild type ALS | 421 QKREFPLGYKTFGEEIPPQYAIQVLDELTKGEAIIATGVGQHQMWAAQYYTYKRPRQWLS | 480 |
| G95A ALS | 421 ............................................................ | 480 |
| | ************************************************************ | |
| wild type ALS | 481 SAGLGAMGFGLPAAAGASVANPGVTVVDIDGDGSFLMNIQELALIRIENLPVKVMVLNNQ | 540 |
| G95A ALS | 481 ............................................................ | 540 |
| | ************************************************************ | |
| wild type ALS | 541 HLGMVVQWEDRFYKANRAHTYLGNPECESEIYPDFVTIAKGFNIPAVRVTKKSEVRAAIK | 600 |
| G95A ALS | 541 ............................................................ | 600 |
| | ************************************************************ | |
| wild type ALS | 601 KMLETPGPYLLDIIVPHQEHVLPMIPSGGAFKDMILDGDGRTVY | 644 |
| G95A ALS | 601 ............................................ | 644 |
| | ******************************************* | |

Fig. 2-1

```
wild type ALS    1 ATGGCTACGACCGCCGCGGGGCCGGGGCCGCGGGCCCTGTCCCGCCGCGGACGGCAAGACC    60
G95A ALS         1 ..........................................................    60
                   ************************************************************ wild type ALS   61 GGCCCGTAAGAACCACCAGCGACACCACGTCCTTCCCGCTCGAGGCCGGGTGGGGCGGCG   120
G95A ALS        61 ..........................................................   120
                   ************************************************************ wild type ALS  121 GCGGTCAGGTGCTCGGCGGTGTCCCGGTCACCCGGCCGTCCCCGGCCGCCGGCCACG     180
G95A ALS       121 ..........................................................   180
                   ************************************************************ wild type ALS  181 CCGCTCCGCCGTGGGGCCGGCCGAGCCCCGCAAGGGCGCGGACATCCTCGTTGGAGGCG   240
G95A ALS       181 ..........................................................   240
                   ************************************************************ wild type ALS  241 CTGGAGCGGTGCGGCGTCAGGACGTGTTCGCCTACCCGGGCGGCGCGTCCATGGAGATC   300
G95A ALS       241 .........................C................................   300
                   ************************ ******************************* wild type ALS  301 CACCAGGCGGCTGACGCGGCTCCCGGTCATCACCAACCACCACCTCTTCCGCCACGAGCAGGGC   360
G95A ALS       301 ..........................................................   360
                   ************************************************************ wild type ALS  361 GAGGCGTTCGCGGGCGTCCGGCGGCTACGCGCGGTGTCCGGCCGCGTCGGGGTCTGCGCC   420
G95A ALS       361 ..........................................................   420
                   ************************************************************ wild type ALS  421 ACCTCCGCCCCGGGGCAACCAACCTCGTGTCCCGGCCGACGCGGCTGCTCGACTCC     480
G95A ALS       421 ..........................................................   480
                   ************************************************************ wild type ALS  481 GTCCCGATGGTCGCCATCACGGGCCAGGTCCCCGCCGCATGATCGGCACCGACGCCTTC   540
G95A ALS       481 ..........................................................   540
                   ************************************************************ wild type ALS  541 CAGGAGACGCCCATAGTCGAGTCACCCGCTCCATCACCAAGCACAATTACCTTGTCTT   600
G95A ALS       541 ..........................................................   600
                   ************************************************************ wild type ALS  601 GATGTGGAGGACATCCCCCGGTCATACAGGAGGCCTTCTTCCTCGGCTCCTCGGGCCGT   660
G95A ALS       601 ..........................................................   660
                   ************************************************************
```

Fig. 2-2

```
wild type ALS  661 CCTGGCCCGGTGCTGCTGGATCGACATCCCCAAGGACATCCAGCAGCAGATGGCCGTGCCGGTC  720
G95A ALS       661 ...............................................................  720
                   *************************************************************** wild type ALS  721 TGGGACACCTGATGAATCTACCAGGGTACACTCGCACGGCTGCCCAAGCCACCCGGGACA     780
G95A ALS       721 ............................................................     780
                   ************************************************************ wild type ALS  781 GAATTGCTTGAGCAGGTCTTGCGTCTGGTTGGCGAGTCACGGCGCCCGATTCTCTATGTC  840
G95A ALS       781 ............................................................  840
                   ************************************************************ wild type ALS  841 GGTGGTGGCTGCTGCTCTGCATCTGGTGACGAATTGCGCTGGTTGTTGAGCTGACTGGTATC  900
G95A ALS       841 ..............................................................  900
                   ************************************************************** wild type ALS  901 CCAGTTACAACCACTCTGATGGGCCTCGCAATTTCCCCAGTGACGACCGTTGTCCCTG    960
G95A ALS       901 ..........................................................    960
                   ********************************************************** wild type ALS  961 CGCATGCTTGGGATGCATGGCCACGGTGTACGCAAATTATGCCGTGGATAAGGCTGACCTG  1020
G95A ALS       961 ............................................................  1020
                   ************************************************************ wild type ALS 1021 TTGCTTGCGTTGGTGTGCGGTTTGATGATCGTGTGACAGGGAAAATTGAGGCTTTTGCA    1080
G95A ALS      1021 ..........................................................    1080
                   ********************************************************** wild type ALS 1081 AGCAGGGCCAAGATGTGCACATTGACATTCGTCAGCAGAGATTGGAAAGAACAAGCAA    1140
G95A ALS      1081 .........................................................    1140
                   ********************************************************* wild type ALS 1141 CCACATGTGTCAATTTGCGCAGATGTTAAGCTTGCTTTACAGGGCTTGAATGCTCTGCTA  1200
G95A ALS      1141 ............................................................  1200
                   ************************************************************ wild type ALS 1201 CAACAGAGCACAACAAAGACAAGTTCTGATTTTAGTGCATGGCACAATGAGTTGGACCAG  1260
G95A ALS      1201 ............................................................  1260
                   ************************************************************ wild type ALS 1261 CAGAAGAGGGAGTTTCCTCTGGGTACAAAAACTTTGGTGAAAGAGATCCCACCGCAATAT  1320
G95A ALS      1261 ............................................................  1320
                   ************************************************************
```

Fig. 2-3

```
wild type ALS  1321 GCCATTCAGGTGTGCTGGATGAGCTGACGAAAGGTGAGGCAATCATGCTACTGGTGTTGGG 1380
G95A ALS       1321 ............................................................ 1380
                    ************************************************************ wild type ALS  1381 CAGGACCAGATGTGGGCGGCACAATATTACACCTACAAGGCGGCCACGCAGTGGCTGTCT 1440
G95A ALS       1381 ............................................................ 1440
                    ************************************************************ wild type ALS  1441 TCGGCTGGTCTGGGGCAATGGGATTTGGGCTGCCTGCTGCAGCTGGTGCTTCTGTGGCT 1500
G95A ALS       1441 ............................................................ 1500
                    ************************************************************ wild type ALS  1501 AACCCAGGTGTCACAGTTGTTGATATTGATGGGGATGGTAGCTTCCTCATGAACATTCAG 1560
G95A ALS       1501 ............................................................ 1560
                    ************************************************************ wild type ALS  1561 GAGCTGGCATTGATCGCATTGAGAACCTCCCTGTGAAGGTGATGGTGTTGAACAACCAA 1620
G95A ALS       1561 ............................................................ 1620
                    ************************************************************ wild type ALS  1621 CATTTGGTATGGTGGTGCAATGGGAGGATAGGTTTTACAAGGCGAATAGGGCGCATACA 1680
G95A ALS       1621 ............................................................ 1680
                    ************************************************************ wild type ALS  1681 TACTTGGGCAACCGGAATGTGAGAGCGAGATATATCCAGATTTTGTGACTATTGCTAAG 1740
G95A ALS       1681 ............................................................ 1740
                    ************************************************************ wild type ALS  1741 GGGTTCAATATTCCTGCAGTCAGTGTAACAACAAGAAGAGTGAAGTCCGTGCCGCCATCAAG 1800
G95A ALS       1741 ............................................................ 1800
                    ************************************************************ wild type ALS  1801 AAGATGCTCGAGACTTCCAGGGCCATACTTGTTGGATATCATCGTCCCGCCACCAGGAGCAT 1860
G95A ALS       1801 ............................................................ 1860
                    ************************************************************ wild type ALS  1861 GTCCTGCCTATGATCCCAAGTGGGGGCGCATTCAAGGACATGATCCTGGATGGTGATGGC 1920
G95A ALS       1861 ............................................................ 1920
                    ************************************************************ wild type ALS  1921 AGGACTGTGTATTAA 1935
G95A ALS       1921 ............... 1935
                    ***************
```

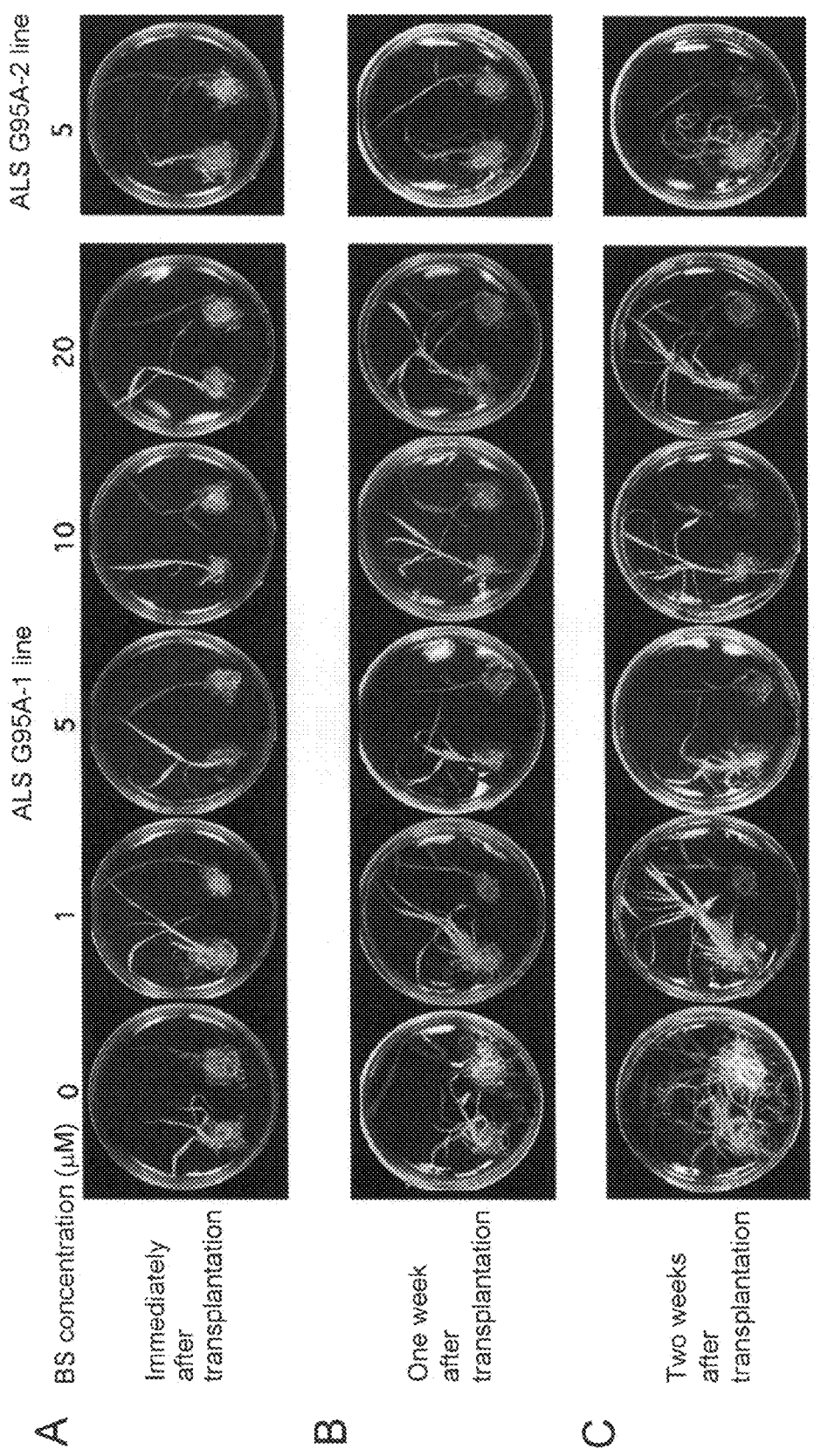

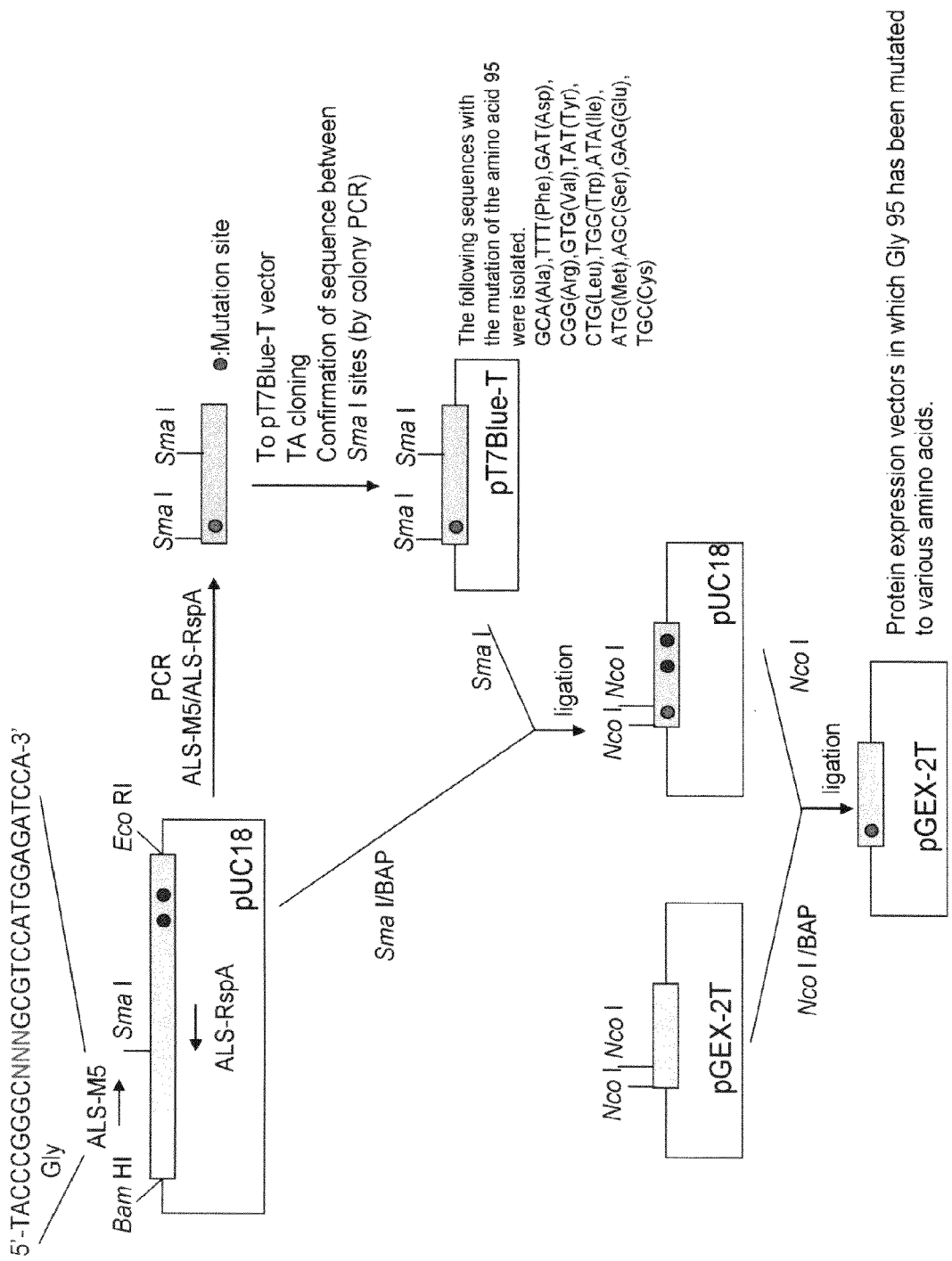

SEQUENCE LISTING

```
<160> NUMBER OF SEQ ID NOS: 39

<210> SEQ ID NO 1
<211> LENGTH: 1935
<212> TYPE: DNA
<213> ORGANISM: Oryza sativa
<220> FEATURE:
<221> NAME/KEY: CDS
<222> LOCATION: (1)..(1935)

<400> SEQUENCE: 1 atg gct acg acc gcc gcg gcc gcg gcc gcc gcc ctg tcc gcc gcc gcg      48
Met Ala Thr Thr Ala Ala Ala Ala Ala Ala Ala Leu Ser Ala Ala Ala
1               5                   10                  15 acg gcc aag acc ggc cgt aag aac cac cag cga cac cac gtc ctt ccc      96
Thr Ala Lys Thr Gly Arg Lys Asn His Gln Arg His His Val Leu Pro
```

```
                    20                  25                  30
gct cga ggc cgg gtg ggg gcg gcg gcg gtc agg tgc tcg gcg gtg tcc    144
Ala Arg Gly Arg Val Gly Ala Ala Ala Val Arg Cys Ser Ala Val Ser
         35                  40                  45 ccg gtc acc ccg ccg tcc ccg gcg ccg ccg gcc acg ccg ctc cgg ccg    192
Pro Val Thr Pro Pro Ser Pro Ala Pro Pro Ala Thr Pro Leu Arg Pro
 50                  55                  60 tgg ggg ccg gcc gag ccc cgc aag ggc gcg gac atc ctc gtg gag gcg    240
Trp Gly Pro Ala Glu Pro Arg Lys Gly Ala Asp Ile Leu Val Glu Ala
 65                  70                  75                  80 ctg gag cgg tgc ggc gtc agc gac gtg ttc gcc tac ccg ggc gcc gcg    288
Leu Glu Arg Cys Gly Val Ser Asp Val Phe Ala Tyr Pro Gly Ala Ala
                 85                  90                  95 tcc atg gag atc cac cag gcg ctg acg cgc tcc ccg gtc atc acc aac    336
Ser Met Glu Ile His Gln Ala Leu Thr Arg Ser Pro Val Ile Thr Asn
            100                 105                 110 cac ctc ttc cgc cac gag cag ggc gag gcg ttc gcg gcg tcc ggg tac    384
His Leu Phe Arg His Glu Gln Gly Glu Ala Phe Ala Ala Ser Gly Tyr
        115                 120                 125 gcg cgc gcg tcc ggc cgc gtc ggg gtc tgc gtc gcc acc tcc ggc ccc    432
Ala Arg Ala Ser Gly Arg Val Gly Val Cys Val Ala Thr Ser Gly Pro
    130                 135                 140 ggg gca acc aac ctc gtg tcc gcg ctc gcc gac gcg ctg ctc gac tcc    480
Gly Ala Thr Asn Leu Val Ser Ala Leu Ala Asp Ala Leu Leu Asp Ser
145                 150                 155                 160 gtc ccg atg gtc gcc atc acg ggc cag gtc ccc cgc cgc atg atc ggc    528
Val Pro Met Val Ala Ile Thr Gly Gln Val Pro Arg Arg Met Ile Gly
                165                 170                 175 acc gac gcc ttc cag gag acg ccc ata gtc gag gtc acc cgc tcc atc    576
Thr Asp Ala Phe Gln Glu Thr Pro Ile Val Glu Val Thr Arg Ser Ile
            180                 185                 190 acc aag cac aat tac ctt gtc ctt gat gtg gag gac atc ccc cgc gtc    624
Thr Lys His Asn Tyr Leu Val Leu Asp Val Glu Asp Ile Pro Arg Val
        195                 200                 205 ata cag gaa gcc ttc ttc ctc gcg tcc tcg ggc cgt cct ggc ccg gtg    672
Ile Gln Glu Ala Phe Phe Leu Ala Ser Ser Gly Arg Pro Gly Pro Val
    210                 215                 220 ctg gtc gac atc ccc aag gac atc cag cag cag atg gcc gtg ccg gtc    720
Leu Val Asp Ile Pro Lys Asp Ile Gln Gln Gln Met Ala Val Pro Val
225                 230                 235                 240 tgg gac acc tcg atg aat cta cca ggg tac atc gca cgc ctg ccc aag    768
Trp Asp Thr Ser Met Asn Leu Pro Gly Tyr Ile Ala Arg Leu Pro Lys
                245                 250                 255 cca ccc gcg aca gaa ttg ctt gag cag gtc ttg cgt ctg gtt ggc gag    816
Pro Pro Ala Thr Glu Leu Leu Glu Gln Val Leu Arg Leu Val Gly Glu
            260                 265                 270 tca cgg cgc ccg att ctc tat gtc ggt ggt ggc tgc tct gca tct ggt    864
Ser Arg Arg Pro Ile Leu Tyr Val Gly Gly Gly Cys Ser Ala Ser Gly
        275                 280                 285 gac gaa ttg cgc tgg ttt gtt gag ctg act ggt atc cca gtt aca acc    912
Asp Glu Leu Arg Trp Phe Val Glu Leu Thr Gly Ile Pro Val Thr Thr
    290                 295                 300 act ctg atg ggc ctc ggc aat ttc ccc agt gac gac ccg ttg tcc ctg    960
Thr Leu Met Gly Leu Gly Asn Phe Pro Ser Asp Asp Pro Leu Ser Leu
305                 310                 315                 320 cgc atg ctt ggg atg cat ggc acg gtg tac gca aat tat gcc gtg gat   1008
Arg Met Leu Gly Met His Gly Thr Val Tyr Ala Asn Tyr Ala Val Asp
                325                 330                 335 aag gct gac ctg ttg ctt gcg ttt ggt gtg cgg ttt gat gat cgt gtg   1056
Lys Ala Asp Leu Leu Leu Ala Phe Gly Val Arg Phe Asp Asp Arg Val
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 340 |     |     |     |     | 345 |     |     |     |     | 350 |     |      |
| aca | ggg | aaa | att | gag | gct | ttt | gca | agc | agg | gcc | aag | att | gtg | cac | att | 1104 |
| Thr | Gly | Lys | Ile | Glu | Ala | Phe | Ala | Ser | Arg | Ala | Lys | Ile | Val | His | Ile |      |
|     |     |     |     | 355 |     |     |     |     | 360 |     |     |     |     | 365 |     |      |
| gac | att | gat | cca | gca | gag | att | gga | aag | aac | aag | caa | cca | cat | gtg | tca | 1152 |
| Asp | Ile | Asp | Pro | Ala | Glu | Ile | Gly | Lys | Asn | Lys | Gln | Pro | His | Val | Ser |      |
|     |     | 370 |     |     |     |     | 375 |     |     |     |     | 380 |     |     |     |      |
| att | tgc | gca | gat | gtt | aag | ctt | gct | tta | cag | ggc | ttg | aat | gct | ctg | cta | 1200 |
| Ile | Cys | Ala | Asp | Val | Lys | Leu | Ala | Leu | Gln | Gly | Leu | Asn | Ala | Leu | Leu |      |
| 385 |     |     |     |     | 390 |     |     |     |     | 395 |     |     |     |     | 400 |      |
| caa | cag | agc | aca | aca | aag | aca | agt | tct | gat | ttt | agt | gca | tgg | cac | aat | 1248 |
| Gln | Gln | Ser | Thr | Thr | Lys | Thr | Ser | Ser | Asp | Phe | Ser | Ala | Trp | His | Asn |      |
|     |     |     |     | 405 |     |     |     |     | 410 |     |     |     |     | 415 |     |      |
| gag | ttg | gac | cag | cag | aag | agg | gag | ttt | cct | ctg | ggg | tac | aaa | act | ttt | 1296 |
| Glu | Leu | Asp | Gln | Gln | Lys | Arg | Glu | Phe | Pro | Leu | Gly | Tyr | Lys | Thr | Phe |      |
|     |     |     | 420 |     |     |     |     | 425 |     |     |     |     | 430 |     |     |      |
| ggt | gaa | gag | atc | cca | ccg | caa | tat | gcc | att | cag | gtg | ctg | gat | gag | ctg | 1344 |
| Gly | Glu | Glu | Ile | Pro | Pro | Gln | Tyr | Ala | Ile | Gln | Val | Leu | Asp | Glu | Leu |      |
|     |     | 435 |     |     |     |     | 440 |     |     |     |     | 445 |     |     |     |      |
| acg | aaa | ggt | gag | gca | atc | atc | gct | act | ggt | gtt | ggg | cag | cac | cag | atg | 1392 |
| Thr | Lys | Gly | Glu | Ala | Ile | Ile | Ala | Thr | Gly | Val | Gly | Gln | His | Gln | Met |      |
| 450 |     |     |     |     | 455 |     |     |     |     | 460 |     |     |     |     |     |      |
| tgg | gcg | gca | caa | tat | tac | acc | tac | aag | cgg | cca | cgg | cag | tgg | ctg | tct | 1440 |
| Trp | Ala | Ala | Gln | Tyr | Tyr | Thr | Tyr | Lys | Arg | Pro | Arg | Gln | Trp | Leu | Ser |      |
| 465 |     |     |     |     | 470 |     |     |     |     | 475 |     |     |     |     | 480 |      |
| tcg | gct | ggt | ctg | ggc | gca | atg | gga | ttt | ggg | ctg | cct | gct | gca | gct | ggt | 1488 |
| Ser | Ala | Gly | Leu | Gly | Ala | Met | Gly | Phe | Gly | Leu | Pro | Ala | Ala | Ala | Gly |      |
|     |     |     |     | 485 |     |     |     |     | 490 |     |     |     |     | 495 |     |      |
| gct | tct | gtg | gct | aac | cca | ggt | gtc | aca | gtt | gtt | gat | att | gat | ggg | gat | 1536 |
| Ala | Ser | Val | Ala | Asn | Pro | Gly | Val | Thr | Val | Val | Asp | Ile | Asp | Gly | Asp |      |
|     |     ом |     500 |     |     |     |     | 505 |     |     |     |     | 510 |     |     |      |
| ggt | agc | ttc | ctc | atg | aac | att | cag | gag | ctg | gca | ttg | atc | cgc | att | gag | 1584 |
| Gly | Ser | Phe | Leu | Met | Asn | Ile | Gln | Glu | Leu | Ala | Leu | Ile | Arg | Ile | Glu |      |
|     |     | 515 |     |     |     |     | 520 |     |     |     |     | 525 |     |     |     |      |
| aac | ctc | cct | gtg | aag | gtg | atg | gtg | ttg | aac | aac | caa | cat | ttg | ggt | atg | 1632 |
| Asn | Leu | Pro | Val | Lys | Val | Met | Val | Leu | Asn | Asn | Gln | His | Leu | Gly | Met |      |
|     |     | 530 |     |     |     |     | 535 |     |     |     |     | 540 |     |     |     |      |
| gtg | gtg | caa | tgg | gag | gat | agg | ttt | tac | aag | gcg | aat | agg | gcg | cat | aca | 1680 |
| Val | Val | Gln | Trp | Glu | Asp | Arg | Phe | Tyr | Lys | Ala | Asn | Arg | Ala | His | Thr |      |
| 545 |     |     |     |     | 550 |     |     |     |     | 555 |     |     |     |     | 560 |      |
| tac | ttg | ggc | aac | ccg | gaa | tgt | gag | agc | gag | ata | tat | cca | gat | ttt | gtg | 1728 |
| Tyr | Leu | Gly | Asn | Pro | Glu | Cys | Glu | Ser | Glu | Ile | Tyr | Pro | Asp | Phe | Val |      |
|     |     |     |     | 565 |     |     |     |     | 570 |     |     |     |     | 575 |     |      |
| act | att | gct | aag | ggg | ttc | aat | att | cct | gca | gtc | cgt | gta | aca | aag | aag | 1776 |
| Thr | Ile | Ala | Lys | Gly | Phe | Asn | Ile | Pro | Ala | Val | Arg | Val | Thr | Lys | Lys |      |
|     |     |     | 580 |     |     |     |     | 585 |     |     |     |     | 590 |     |     |      |
| agt | gaa | gtc | cgt | gcc | gcc | atc | aag | aag | atg | ctc | gag | act | cca | ggg | cca | 1824 |
| Ser | Glu | Val | Arg | Ala | Ala | Ile | Lys | Lys | Met | Leu | Glu | Thr | Pro | Gly | Pro |      |
|     |     | 595 |     |     |     |     | 600 |     |     |     |     | 605 |     |     |     |      |
| tac | ttg | ttg | gat | atc | atc | gtc | ccg | cac | cag | gag | cat | gtg | ctg | cct | atg | 1872 |
| Tyr | Leu | Leu | Asp | Ile | Ile | Val | Pro | His | Gln | Glu | His | Val | Leu | Pro | Met |      |
|     | 610 |     |     |     |     | 615 |     |     |     |     | 620 |     |     |     |     |      |
| atc | cca | agt | ggg | ggc | gca | ttc | aag | gac | atg | atc | ctg | gat | ggt | gat | ggc | 1920 |
| Ile | Pro | Ser | Gly | Gly | Ala | Phe | Lys | Asp | Met | Ile | Leu | Asp | Gly | Asp | Gly |      |
| 625 |     |     |     |     | 630 |     |     |     |     | 635 |     |     |     |     | 640 |      |
| agg | act | gtg | tat | taa |     |     |     |     |     |     |     |     |     |     |     | 1935 |
| Arg | Thr | Val | Tyr |     |     |     |     |     |     |     |     |     |     |     |     |      |

<210> SEQ ID NO 2
<211> LENGTH: 644

-continued

```
<212> TYPE: PRT
<213> ORGANISM: Oryza sativa

<400> SEQUENCE: 2

Met Ala Thr Thr Ala Ala Ala Ala Ala Leu Ser Ala Ala
1               5                   10                  15

Thr Ala Lys Thr Gly Arg Lys Asn His Gln Arg His His Val Leu Pro
                20                  25                  30

Ala Arg Gly Arg Val Gly Ala Ala Val Arg Cys Ser Ala Val Ser
        35                  40                  45

Pro Val Thr Pro Pro Ser Pro Ala Pro Pro Ala Thr Pro Leu Arg Pro
        50                  55                  60

Trp Gly Pro Ala Glu Pro Arg Lys Gly Ala Asp Ile Leu Val Glu Ala
65                  70                  75                  80

Leu Glu Arg Cys Gly Val Ser Asp Val Phe Ala Tyr Pro Gly Ala Ala
                85                  90                  95

Ser Met Glu Ile His Gln Ala Leu Thr Arg Ser Pro Val Ile Thr Asn
            100                 105                 110

His Leu Phe Arg His Glu Gln Gly Glu Ala Phe Ala Ala Ser Gly Tyr
        115                 120                 125

Ala Arg Ala Ser Gly Arg Val Gly Val Cys Val Ala Thr Ser Gly Pro
    130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
                165                 170                 175

Thr Asp Ala Phe Gln Glu Thr Pro Ile Val Glu Val Thr Arg Ser Ile
            180                 185                 190

Thr Lys His Asn Tyr Leu Val Leu Asp Val Glu Asp Ile Pro Arg Val
        195                 200                 205

Ile Gln Glu Ala Phe Phe Leu Ala Ser Ser Gly Arg Pro Gly Pro Val
    210                 215                 220

Leu Val Asp Ile Pro Lys Asp Ile Gln Gln Gln Met Ala Val Pro Val
225                 230                 235                 240

Trp Asp Thr Ser Met Asn Leu Pro Gly Tyr Ile Ala Arg Leu Pro Lys
                245                 250                 255

Pro Pro Ala Thr Glu Leu Leu Glu Gln Val Leu Arg Leu Val Gly Glu
            260                 265                 270

Ser Arg Arg Pro Ile Leu Tyr Val Gly Gly Cys Ser Ala Ser Gly
        275                 280                 285

Asp Glu Leu Arg Trp Phe Val Glu Leu Thr Gly Ile Pro Val Thr Thr
    290                 295                 300

Thr Leu Met Gly Leu Gly Asn Phe Pro Ser Asp Asp Pro Leu Ser Leu
305                 310                 315                 320

Arg Met Leu Gly Met His Gly Thr Val Tyr Ala Asn Tyr Ala Val Asp
                325                 330                 335

Lys Ala Asp Leu Leu Leu Ala Phe Gly Val Arg Phe Asp Asp Arg Val
            340                 345                 350

Thr Gly Lys Ile Glu Ala Phe Ala Ser Arg Ala Lys Ile Val His Ile
        355                 360                 365

Asp Ile Asp Pro Ala Glu Ile Gly Lys Asn Lys Gln Pro His Val Ser
    370                 375                 380

Ile Cys Ala Asp Val Lys Leu Ala Leu Gln Gly Leu Asn Ala Leu Leu
385                 390                 395                 400
```

```
Gln Gln Ser Thr Thr Lys Thr Ser Ser Asp Phe Ser Ala Trp His Asn
            405                 410                 415

Glu Leu Asp Gln Gln Lys Arg Glu Phe Pro Leu Gly Tyr Lys Thr Phe
        420                 425                 430

Gly Glu Glu Ile Pro Pro Gln Tyr Ala Ile Gln Val Leu Asp Glu Leu
        435                 440                 445

Thr Lys Gly Glu Ala Ile Ile Ala Thr Gly Val Gly Gln His Gln Met
    450                 455                 460

Trp Ala Ala Gln Tyr Tyr Thr Tyr Lys Arg Pro Arg Gln Trp Leu Ser
465                 470                 475                 480

Ser Ala Gly Leu Gly Ala Met Gly Phe Gly Leu Pro Ala Ala Ala Gly
                485                 490                 495

Ala Ser Val Ala Asn Pro Gly Val Thr Val Val Asp Ile Asp Gly Asp
            500                 505                 510

Gly Ser Phe Leu Met Asn Ile Gln Glu Leu Ala Leu Ile Arg Ile Glu
        515                 520                 525

Asn Leu Pro Val Lys Val Met Val Leu Asn Asn Gln His Leu Gly Met
    530                 535                 540

Val Val Gln Trp Glu Asp Arg Phe Tyr Lys Ala Asn Arg Ala His Thr
545                 550                 555                 560

Tyr Leu Gly Asn Pro Glu Cys Glu Ser Glu Ile Tyr Pro Asp Phe Val
                565                 570                 575

Thr Ile Ala Lys Gly Phe Asn Ile Pro Ala Val Arg Val Thr Lys Lys
            580                 585                 590

Ser Glu Val Arg Ala Ala Ile Lys Lys Met Leu Glu Thr Pro Gly Pro
        595                 600                 605

Tyr Leu Leu Asp Ile Ile Val Pro His Gln Glu His Val Leu Pro Met
    610                 615                 620

Ile Pro Ser Gly Gly Ala Phe Lys Asp Met Ile Leu Asp Gly Asp Gly
625                 630                 635                 640

Arg Thr Val Tyr

<210> SEQ ID NO 3
<211> LENGTH: 638
<212> TYPE: PRT
<213> ORGANISM: Zea mays

<400> SEQUENCE: 3

Met Ala Thr Ala Ala Thr Ala Ala Ala Leu Thr Gly Ala Thr Thr
1               5                   10                  15

Ala Thr Pro Lys Ser Arg Arg Ala His His Leu Ala Thr Arg Arg
                20                  25                  30

Ala Leu Ala Ala Pro Ile Arg Cys Ser Ala Leu Ser Arg Ala Thr Pro
            35                  40                  45

Thr Ala Pro Pro Ala Thr Pro Leu Arg Pro Trp Gly Pro Asn Glu Pro
    50                  55                  60

Arg Lys Gly Ser Asp Ile Leu Val Glu Ala Leu Glu Arg Cys Gly Val
65                  70                  75                  80

Arg Asp Val Phe Ala Tyr Pro Gly Ala Ala Ser Met Glu Ile His Gln
                85                  90                  95

Ala Leu Thr Arg Ser Pro Val Ile Ala Asn His Leu Phe Arg His Glu
            100                 105                 110

Gln Gly Glu Ala Phe Ala Ala Ser Ala Tyr Ala Arg Ser Ser Gly Arg
        115                 120                 125

Val Gly Val Cys Ile Ala Thr Ser Gly Pro Gly Ala Thr Asn Leu Val
```

```
            130                 135                 140
Ser Ala Leu Ala Asp Ala Leu Leu Asp Ser Val Pro Met Val Ala Ile
145                 150                 155                 160

Thr Gly Gln Val Pro Arg Arg Met Ile Gly Thr Asp Ala Phe Gln Glu
                165                 170                 175

Thr Pro Ile Val Glu Val Thr Arg Ser Ile Thr Lys His Asn Tyr Leu
                180                 185                 190

Val Leu Asp Val Asp Asp Ile Pro Arg Val Val Gln Glu Ala Phe Phe
                195                 200                 205

Leu Ala Ser Ser Gly Arg Pro Gly Pro Val Leu Val Asp Ile Pro Lys
                210                 215                 220

Asp Ile Gln Gln Gln Met Ala Val Pro Ala Trp Asp Thr Pro Met Ser
225                 230                 235                 240

Leu Pro Gly Tyr Ile Ala Arg Leu Pro Lys Pro Pro Ala Thr Glu Phe
                245                 250                 255

Leu Glu Gln Val Leu Arg Leu Val Gly Glu Ser Arg Arg Pro Val Leu
                260                 265                 270

Tyr Val Gly Gly Gly Cys Ala Ala Ser Gly Glu Glu Leu Cys Arg Phe
                275                 280                 285

Val Glu Leu Thr Gly Ile Pro Val Thr Thr Thr Leu Met Gly Leu Gly
290                 295                 300

Asn Phe Pro Ser Asp Asp Pro Leu Ser Leu Arg Met Leu Gly Met His
305                 310                 315                 320

Gly Thr Val Tyr Ala Asn Tyr Ala Val Asp Lys Ala Asp Leu Leu Leu
                325                 330                 335

Ala Phe Gly Val Arg Phe Asp Asp Arg Val Thr Gly Lys Ile Glu Ala
                340                 345                 350

Phe Ala Gly Arg Ala Lys Ile Val His Ile Asp Ile Asp Pro Ala Glu
                355                 360                 365

Ile Gly Lys Asn Lys Gln Pro His Val Ser Ile Cys Ala Asp Val Lys
                370                 375                 380

Leu Ala Leu Gln Gly Met Asn Thr Leu Leu Glu Gly Ser Thr Ser Lys
385                 390                 395                 400

Lys Ser Phe Asp Phe Gly Ser Trp His Asp Glu Leu Asp Gln Gln Lys
                405                 410                 415

Arg Glu Phe Pro Leu Gly Tyr Lys Ile Phe Asn Glu Ile Gln Pro
                420                 425                 430

Gln Tyr Ala Ile Gln Val Leu Asp Glu Leu Thr Lys Gly Glu Ala Ile
                435                 440                 445

Ile Ala Thr Gly Val Gly Gln His Gln Met Trp Ala Ala Gln Tyr Tyr
450                 455                 460

Thr Tyr Lys Arg Pro Arg Gln Trp Leu Ser Ser Ala Gly Leu Gly Ala
465                 470                 475                 480

Met Gly Phe Gly Leu Pro Ala Ala Ala Gly Ala Ala Val Ala Asn Pro
                485                 490                 495

Gly Val Thr Val Val Asp Ile Asp Gly Asp Gly Ser Phe Leu Met Asn
                500                 505                 510

Ile Gln Glu Leu Ala Met Ile Arg Ile Glu Asn Leu Pro Val Lys Val
                515                 520                 525

Phe Val Leu Asn Asn Gln His Leu Gly Met Val Val Gln Trp Glu Asp
                530                 535                 540

Arg Phe Tyr Lys Ala Asn Arg Ala His Thr Phe Leu Gly Asn Pro Glu
545                 550                 555                 560
```

-continued

```
Asn Glu Ser Glu Ile Tyr Pro Asp Phe Val Ala Ile Ala Lys Gly Phe
            565                 570                 575
Asn Ile Pro Ala Val Arg Val Thr Lys Lys Ser Glu Val His Ala Ala
        580                 585                 590
Ile Lys Lys Met Leu Glu Ala Pro Gly Pro Tyr Leu Leu Asp Ile Ile
    595                 600                 605
Val Pro His Gln Glu His Val Leu Pro Met Ile Pro Ser Gly Gly Ala
610                 615                 620
Phe Lys Asp Met Ile Leu Asp Gly Asp Gly Arg Thr Val Tyr
625                 630                 635

<210> SEQ ID NO 4
<211> LENGTH: 638
<212> TYPE: PRT
<213> ORGANISM: Zea mays

<400> SEQUENCE: 4

Met Ala Thr Ala Ala Ala Ser Thr Ala Leu Thr Gly Ala Thr Thr
1               5                   10                  15
Ala Ala Pro Lys Ala Arg Arg Ala His Leu Leu Ala Thr Arg Arg
            20                  25                  30
Ala Leu Ala Ala Pro Ile Arg Cys Ser Ala Ala Ser Pro Ala Met Pro
        35                  40                  45
Met Ala Pro Pro Ala Thr Pro Leu Arg Pro Trp Gly Pro Thr Asp Pro
    50                  55                  60
Arg Lys Gly Ala Asp Ile Leu Val Glu Ser Leu Glu Arg Cys Gly Val
65                  70                  75                  80
Arg Asp Val Phe Ala Tyr Pro Gly Ala Ala Ser Met Glu Ile His Gln
                85                  90                  95
Ala Leu Thr Arg Ser Pro Val Ile Ala Asn His Leu Phe Arg His Glu
            100                 105                 110
Gln Gly Glu Ala Phe Ala Ala Ser Gly Tyr Ala Arg Ser Ser Gly Arg
        115                 120                 125
Val Gly Val Cys Ile Ala Thr Ser Gly Pro Gly Ala Thr Asn Leu Val
    130                 135                 140
Ser Ala Leu Ala Asp Ala Leu Leu Asp Ser Val Pro Met Val Ala Ile
145                 150                 155                 160
Thr Gly Gln Val Pro Arg Arg Met Ile Gly Thr Asp Ala Phe Gln Glu
                165                 170                 175
Thr Pro Ile Val Glu Val Thr Arg Ser Ile Thr Lys His Asn Tyr Leu
            180                 185                 190
Val Leu Asp Val Asp Asp Ile Pro Arg Val Val Gln Glu Ala Phe Phe
        195                 200                 205
Leu Ala Ser Ser Gly Arg Pro Gly Pro Val Leu Val Asp Ile Pro Lys
    210                 215                 220
Asp Ile Gln Gln Gln Met Ala Val Pro Val Trp Asp Lys Pro Met Ser
225                 230                 235                 240
Leu Pro Gly Tyr Ile Ala Arg Leu Pro Lys Pro Pro Ala Thr Glu Leu
                245                 250                 255
Leu Glu Gln Val Leu Arg Leu Val Gly Glu Ser Arg Arg Pro Val Leu
            260                 265                 270
Tyr Val Gly Gly Gly Cys Ala Ala Ser Gly Glu Glu Leu Arg Arg Phe
        275                 280                 285
Val Glu Leu Thr Gly Ile Pro Val Thr Thr Thr Leu Met Gly Leu Gly
    290                 295                 300
```

```
Asn Phe Pro Ser Asp Asp Pro Leu Ser Leu Arg Met Leu Gly Met His
305                 310                 315                 320

Gly Thr Val Tyr Ala Asn Tyr Ala Val Asp Lys Ala Asp Leu Leu Leu
            325                 330                 335

Ala Leu Gly Val Arg Phe Asp Asp Arg Val Thr Gly Lys Ile Glu Ala
        340                 345                 350

Phe Ala Ser Arg Ala Lys Ile Val His Val Asp Ile Asp Pro Ala Glu
    355                 360                 365

Ile Gly Lys Asn Lys Gln Pro His Val Ser Ile Cys Ala Asp Val Lys
370                 375                 380

Leu Ala Leu Gln Gly Met Asn Ala Leu Leu Glu Gly Ser Thr Ser Lys
385                 390                 395                 400

Lys Ser Phe Asp Phe Gly Ser Trp Asn Asp Glu Leu Asp Gln Gln Lys
                405                 410                 415

Arg Glu Phe Pro Leu Gly Tyr Lys Thr Ser Asn Glu Glu Ile Gln Pro
            420                 425                 430

Gln Tyr Ala Ile Gln Val Leu Asp Glu Leu Thr Lys Gly Glu Ala Ile
        435                 440                 445

Ile Gly Thr Gly Val Gly Gln His Gln Met Trp Ala Ala Gln Tyr Tyr
    450                 455                 460

Thr Tyr Lys Arg Pro Arg Gln Trp Leu Ser Ser Ala Gly Leu Gly Ala
465                 470                 475                 480

Met Gly Phe Gly Leu Pro Ala Ala Gly Ala Ser Val Ala Asn Pro
                485                 490                 495

Gly Val Thr Val Val Asp Ile Asp Gly Asp Gly Ser Phe Leu Met Asn
            500                 505                 510

Val Gln Glu Leu Ala Met Ile Arg Ile Glu Asn Leu Pro Val Lys Val
        515                 520                 525

Phe Val Leu Asn Asn Gln His Leu Gly Met Val Val Gln Trp Glu Asp
    530                 535                 540

Arg Phe Tyr Lys Ala Asn Arg Ala His Thr Tyr Leu Gly Asn Pro Glu
545                 550                 555                 560

Asn Glu Ser Glu Ile Tyr Pro Asp Phe Val Thr Ile Ala Lys Gly Phe
                565                 570                 575

Asn Ile Pro Ala Val Arg Val Thr Lys Lys Asn Glu Val Arg Ala Ala
            580                 585                 590

Ile Lys Lys Met Leu Glu Thr Pro Gly Pro Tyr Leu Leu Asp Ile Ile
        595                 600                 605

Val Pro His Gln Glu His Val Leu Pro Met Ile Pro Ser Gly Gly Ala
610                 615                 620

Phe Lys Asp Met Ile Leu Asp Gly Asp Gly Arg Thr Val Tyr
625                 630                 635

<210> SEQ ID NO 5
<211> LENGTH: 598
<212> TYPE: PRT
<213> ORGANISM: Triticum aestivum

<400> SEQUENCE: 5

Ala Ala Ser Pro Ala Ala Thr Ser Ala Ala Pro Pro Ala Thr Ala Leu
1               5                   10                  15

Arg Pro Trp Gly Pro Ser Glu Pro Arg Lys Gly Ala Asp Ile Leu Val
            20                  25                  30

Glu Ala Leu Glu Arg Cys Gly Ile Val Asp Val Phe Ala Tyr Pro Gly
        35                  40                  45
```

```
Ala Ala Ser Met Glu Ile His Gln Ala Leu Thr Arg Ser Pro Val Ile
 50                  55                  60

Thr Asn His Leu Phe Arg His Glu Gln Gly Glu Ala Phe Ala Ala Ser
 65                  70                  75                  80

Gly Tyr Ala Arg Ala Ser Gly Arg Val Gly Val Cys Val Ala Thr Ser
                 85                  90                  95

Gly Pro Gly Ala Thr Asn Leu Val Ser Ala Leu Ala Asp Ala Leu Leu
            100                 105                 110

Asp Ser Ile Pro Met Val Ala Ile Thr Gly Gln Val Pro Arg Arg Met
        115                 120                 125

Ile Gly Thr Asp Ala Phe Gln Glu Thr Pro Ile Val Glu Val Thr Arg
    130                 135                 140

Ser Ile Thr Lys His Asn Tyr Leu Val Leu Asp Val Glu Asp Ile Pro
145                 150                 155                 160

Arg Val Ile Gln Glu Ala Phe Phe Leu Ala Ser Ser Arg Pro Gly
                165                 170                 175

Pro Val Leu Val Asp Ile Pro Lys Asp Ile Gln Gln Met Ala Val
            180                 185                 190

Pro Val Trp Asp Thr Pro Met Ser Leu Pro Gly Tyr Ile Ala Arg Leu
        195                 200                 205

Pro Lys Pro Pro Ser Thr Glu Ser Leu Glu Gln Val Leu Arg Leu Val
    210                 215                 220

Gly Glu Ser Arg Arg Pro Ile Leu Tyr Val Gly Gly Cys Ala Ala
225                 230                 235                 240

Ser Gly Glu Glu Leu Arg Arg Phe Val Glu Leu Thr Gly Ile Pro Val
                245                 250                 255

Thr Thr Thr Leu Met Gly Leu Gly Asn Phe Pro Ser Asp Asp Pro Leu
            260                 265                 270

Ser Leu Arg Met Leu Gly Met His Gly Thr Val Tyr Ala Asn Tyr Ala
        275                 280                 285

Val Asp Lys Ala Asp Leu Leu Leu Ala Phe Gly Val Arg Phe Asp Asp
    290                 295                 300

Arg Val Thr Gly Lys Ile Glu Ala Phe Ala Ser Arg Ser Lys Ile Val
305                 310                 315                 320

His Ile Asp Ile Asp Pro Ala Glu Ile Gly Lys Asn Lys Gln Pro His
                325                 330                 335

Val Ser Ile Cys Ala Asp Val Lys Leu Ala Leu Gln Gly Leu Asn Asp
            340                 345                 350

Leu Leu Asn Gly Ser Lys Ala Gln Gln Gly Leu Asp Phe Gly Pro Trp
        355                 360                 365

His Lys Glu Leu Asp Gln Gln Lys Arg Glu Phe Pro Leu Gly Phe Lys
    370                 375                 380

Thr Phe Gly Glu Ala Ile Pro Pro Gln Tyr Ala Ile Gln Val Leu Asp
385                 390                 395                 400

Glu Leu Thr Lys Gly Glu Ala Ile Ile Ala Thr Gly Val Gly Gln His
                405                 410                 415

Gln Met Trp Ala Ala Gln Tyr Tyr Thr Tyr Lys Arg Pro Arg Gln Trp
            420                 425                 430

Leu Ser Ser Ser Gly Leu Gly Ala Met Gly Phe Gly Leu Pro Ala Ala
        435                 440                 445

Ala Gly Ala Ala Val Ala Asn Pro Gly Val Thr Val Val Asp Ile Asp
    450                 455                 460

Gly Asp Gly Ser Phe Leu Met Asn Ile Gln Glu Leu Ala Leu Ile Arg
465                 470                 475                 480
```

-continued

Ile Glu Asn Leu Pro Val Lys Val Met Ile Leu Asn Asn Gln His Leu
            485                 490                 495

Gly Met Val Val Gln Trp Glu Asp Arg Phe Tyr Lys Ala Asn Arg Ala
        500                 505                 510

His Thr Tyr Leu Gly Asn Pro Glu Asn Glu Ser Glu Ile Tyr Pro Asp
        515                 520                 525

Phe Val Thr Ile Ala Lys Gly Phe Asn Val Pro Ala Val Arg Val Thr
        530                 535                 540

Lys Lys Ser Glu Val Thr Ala Ala Ile Lys Lys Met Leu Glu Thr Pro
545                 550                 555                 560

Gly Pro Tyr Leu Leu Asp Ile Ile Val Pro His Gln Glu His Val Leu
                565                 570                 575

Pro Met Ile Pro Ser Gly Gly Ala Phe Lys Asp Met Ile Met Glu Gly
                580                 585                 590

Asp Gly Arg Thr Ser Tyr
            595

<210> SEQ ID NO 6
<211> LENGTH: 598
<212> TYPE: PRT
<213> ORGANISM: Triticum aestivum

<400> SEQUENCE: 6

Ala Ala Ser Pro Ala Ala Thr Ser Val Ala Pro Pro Ala Thr Ala Leu
1               5                   10                  15

Arg Pro Trp Gly Pro Ser Glu Pro Arg Lys Gly Ala Asp Ile Leu Val
            20                  25                  30

Glu Ala Leu Glu Arg Cys Gly Ile Val Asp Val Phe Ala Tyr Pro Gly
        35                  40                  45

Ala Ala Ser Met Glu Ile His Gln Ala Leu Thr Arg Ser Pro Val Ile
    50                  55                  60

Thr Asn His Leu Phe Arg His Glu Gln Gly Glu Ala Phe Ala Ala Ser
65              70                  75                  80

Gly Tyr Ala Arg Ala Ser Gly Arg Val Gly Val Cys Val Ala Thr Ser
                85                  90                  95

Gly Pro Gly Ala Thr Asn Leu Val Ser Ala Leu Ala Asp Ala Leu Leu
            100                 105                 110

Asp Ser Ile Pro Met Val Ala Ile Thr Gly Gln Val Pro Arg Arg Met
        115                 120                 125

Ile Gly Thr Asp Ala Phe Gln Glu Thr Pro Ile Val Glu Val Thr Arg
    130                 135                 140

Ser Ile Thr Lys His Asn Tyr Leu Val Leu Asp Val Glu Asp Ile Pro
145                 150                 155                 160

Arg Val Ile Gln Glu Ala Phe Phe Leu Ala Ser Ser Gly Arg Pro Gly
                165                 170                 175

Pro Val Leu Val Asp Ile Pro Lys Asp Ile Gln Gln Gln Met Ala Val
            180                 185                 190

Pro Val Trp Asp Thr Pro Met Ser Leu Pro Gly Tyr Ile Ala Arg Leu
        195                 200                 205

Pro Lys Pro Pro Ser Thr Glu Ser Leu Glu Gln Val Leu Arg Leu Val
    210                 215                 220

Gly Glu Ser Arg Arg Pro Ile Leu Tyr Val Gly Gly Gly Cys Ala Ala
225                 230                 235                 240

Ser Gly Glu Glu Leu Arg Arg Phe Val Glu Leu Thr Gly Ile Pro Val
                245                 250                 255

```
Thr Thr Thr Leu Met Gly Leu Gly Asn Phe Pro Ser Asp Asp Pro Leu
            260                 265                 270

Ser Leu Arg Met Leu Gly Met His Gly Thr Val Tyr Ala Asn Tyr Ala
        275                 280                 285

Val Asp Lys Ala Asp Leu Leu Ala Phe Gly Val Arg Phe Asp Asp
    290                 295                 300

Arg Val Thr Gly Lys Ile Glu Ala Phe Ala Ser Arg Ser Lys Ile Val
305                 310                 315                 320

His Ile Asp Ile Asp Pro Ala Glu Ile Gly Lys Asn Lys Gln Pro His
            325                 330                 335

Val Ser Ile Cys Ala Asp Val Lys Leu Ala Leu Gln Gly Leu Asn Ala
        340                 345                 350

Leu Leu Asn Gly Ser Lys Ala Gln Gln Gly Leu Asp Phe Gly Pro Trp
    355                 360                 365

His Lys Glu Leu Asp Gln Gln Lys Arg Glu Phe Pro Leu Gly Phe Lys
        370                 375                 380

Thr Phe Gly Glu Ala Ile Pro Pro Gln Tyr Ala Ile Gln Val Leu Asp
385                 390                 395                 400

Glu Leu Thr Lys Gly Glu Ala Ile Ile Ala Thr Gly Val Gly Gln His
            405                 410                 415

Gln Met Trp Ala Ala Gln Tyr Tyr Thr Tyr Lys Arg Pro Arg Gln Trp
        420                 425                 430

Leu Ser Ser Gly Leu Gly Ala Met Gly Phe Gly Leu Pro Ala Ala
    435                 440                 445

Ala Gly Ala Ala Val Ala Asn Pro Gly Val Thr Val Val Asp Ile Asp
    450                 455                 460

Gly Asp Gly Ser Phe Leu Met Asn Ile Gln Glu Leu Ala Leu Ile Arg
465                 470                 475                 480

Ile Glu Asn Leu Pro Val Lys Val Met Ile Leu Asn Asn Gln His Leu
            485                 490                 495

Gly Met Val Val Gln Trp Glu Asp Arg Phe Tyr Lys Ala Asn Arg Ala
        500                 505                 510

His Thr Tyr Leu Gly Asn Pro Glu Asn Glu Ser Glu Ile Tyr Pro Asp
    515                 520                 525

Phe Val Thr Ile Ala Lys Gly Phe Asn Val Pro Ala Val Arg Val Thr
    530                 535                 540

Lys Lys Ser Glu Val Thr Ala Ala Ile Lys Lys Met Leu Glu Thr Pro
545                 550                 555                 560

Gly Pro Tyr Leu Leu Asp Ile Ile Val Pro His Gln Glu His Val Leu
            565                 570                 575

Pro Met Ile Pro Ser Gly Gly Ala Phe Lys Asp Met Ile Met Glu Gly
        580                 585                 590

Asp Gly Arg Thr Ser Tyr
            595

<210> SEQ ID NO 7
<211> LENGTH: 659
<212> TYPE: PRT
<213> ORGANISM: Gossypium hirsutum

<400> SEQUENCE: 7

Met Ala Ala Ala Thr Ser Asn Ser Ala Leu Pro Lys Leu Ser Thr Leu
1               5                   10                  15

Thr Ser Ser Phe Lys Ser Ser Ile Pro Ile Ser Lys Ser Ser Leu Pro
            20                  25                  30
```

```
Phe Ser Thr Thr Pro Gln Lys Pro Thr Pro Tyr Arg Ser Phe Asp Val
        35                  40                  45

Ser Cys Ser Leu Ser His Ala Ser Ser Asn Pro Arg Ser Ala Ala Ala
 50                  55                  60

Ser Val Thr Gln Lys Thr Ala Pro Pro His Tyr Phe Ile Ser Arg Tyr
 65                  70                  75                  80

Ala Asp Asp Glu Pro Arg Lys Gly Ala Asp Ile Leu Val Glu Ala Leu
                 85                  90                  95

Glu Arg Glu Gly Val Lys Asp Val Phe Ala Tyr Pro Gly Ala Ala Ser
                100                 105                 110

Met Glu Ile His Gln Ala Leu Thr Arg Ser Lys Ile Ile Arg Asn Val
            115                 120                 125

Leu Pro Arg His Glu Gln Gly Gly Val Phe Ala Ala Glu Gly Tyr Ala
        130                 135                 140

Arg Ser Ser Gly Ile Ser Gly Val Cys Ile Ala Thr Ser Gly Pro Gly
145                 150                 155                 160

Ala Thr Asn Leu Val Ser Gly Leu Ala Asp Ala Met Leu Asp Ser Ile
                165                 170                 175

Pro Leu Val Ala Ile Thr Gly Gln Val Pro Arg Arg Met Ile Gly Thr
            180                 185                 190

Asp Ala Phe Gln Glu Thr Pro Ile Val Glu Val Thr Arg Ser Ile Thr
        195                 200                 205

Lys His Asn Tyr Leu Val Leu Asp Val Asp Asp Ile Pro Arg Ile Val
    210                 215                 220

Ser Glu Ala Phe Phe Leu Ala Ser Ser Gly Arg Pro Gly Pro Val Leu
225                 230                 235                 240

Ile Asp Val Pro Lys Asp Ile Gln Gln Gln Leu Ala Val Pro Lys Trp
                245                 250                 255

Asn His Ser Leu Arg Leu Pro Gly Tyr Leu Ser Arg Leu Pro Lys Ala
            260                 265                 270

Pro Ala Glu Ala His Leu Glu Gln Ile Val Arg Leu Val Ser Glu Ser
        275                 280                 285

Lys Lys Pro Val Leu Tyr Val Gly Gly Gly Cys Leu Asn Ser Ser Glu
    290                 295                 300

Glu Leu Lys Arg Phe Val Glu Leu Thr Gly Ile Pro Val Ala Ser Thr
305                 310                 315                 320

Leu Met Gly Leu Gly Ala Phe Pro Ile Ser Asp Glu Leu Ser Leu Gln
                325                 330                 335

Met Leu Gly Met His Gly Thr Val Tyr Ala Asn Tyr Ala Val Asp Lys
            340                 345                 350

Ser Asp Leu Leu Leu Ala Phe Gly Val Arg Phe Asp Asp Arg Val Thr
        355                 360                 365

Gly Lys Leu Glu Ala Phe Ala Ser Arg Ala Lys Ile Val His Ile Asp
    370                 375                 380

Ile Asp Ser Ala Glu Ile Gly Lys Asn Lys Gln Pro His Met Ser Val
385                 390                 395                 400

Cys Ser Asp Val Lys Leu Ala Leu Gln Gly Ile Asn Lys Ile Leu Glu
                405                 410                 415

Thr Thr Gly Ala Lys Leu Asn Leu Asp Tyr Ser Glu Trp Arg Gln Glu
            420                 425                 430

Leu Asn Glu Gln Lys Leu Lys Phe Pro Leu Ser Tyr Lys Thr Phe Gly
        435                 440                 445

Glu Ala Ile Pro Pro Gln Tyr Ala Ile Gln Val Leu Asp Glu Leu Thr
```

```
                    450                 455                 460
Gly Gly Asn Ala Ile Ile Ser Thr Gly Val Gly Gln His Gln Met Trp
465                 470                 475                 480

Ala Ala Gln Phe Tyr Lys Tyr Lys Pro Arg Gln Trp Leu Thr Ser
                485                 490                 495

Gly Gly Leu Gly Ala Met Gly Phe Gly Leu Pro Ala Ala Ile Gly Ala
                500                 505                 510

Ala Val Ala Asn Pro Glu Ala Val Val Asp Ile Asp Gly Asp
                515                 520                 525

Ser Phe Ile Met Asn Val Gln Glu Leu Ala Thr Met Arg Val Glu Asn
                530                 535                 540

Leu Pro Val Lys Ile Leu Leu Asn Asn Gln His Leu Gly Met Val
545                 550                 555                 560

Val Gln Trp Glu Asp Arg Phe Tyr Lys Ala Asn Arg Ala His Thr Tyr
                565                 570                 575

Leu Gly Asp Pro Ser Asn Glu Ser Glu Ile Phe Pro Asn Met Leu Lys
                580                 585                 590

Phe Ala Glu Ala Cys Gly Ile Pro Ala Ala Arg Val Thr Lys Lys Glu
                595                 600                 605

Asp Leu Lys Ala Ala Ile Gln Lys Met Leu Asp Thr Pro Gly Pro Tyr
                610                 615                 620

Leu Leu Asp Val Ile Val Pro His Gln Glu His Val Leu Pro Met Ile
625                 630                 635                 640

Pro Ser Gly Gly Ala Phe Lys Asp Val Ile Thr Glu Gly Asp Gly Arg
                645                 650                 655

Thr Gln Tyr

<210> SEQ ID NO 8
<211> LENGTH: 659
<212> TYPE: PRT
<213> ORGANISM: Gossypium hirsutum

<400> SEQUENCE: 8

Met Ala Ala Ala Thr Ala Asn Ser Ala Leu Pro Lys Leu Ser Thr Leu
1               5                   10                  15

Thr Ser Ser Phe Lys Ser Ser Ile Pro Ile Ser Lys Ser Ser Leu Pro
                20                  25                  30

Phe Ser Thr Thr Pro Gln Lys Pro Thr Pro Tyr Arg Ser Phe Asp Val
            35                  40                  45

Ser Cys Ser Leu Ser His Ala Ser Ser Asn Pro Arg Ser Ala Ala Thr
        50                  55                  60

Ser Val Thr Pro Lys Asn Ala Pro Pro His Asp Phe Ile Ser Arg Tyr
65                  70                  75                  80

Ala Asp Asp Glu Pro Arg Lys Gly Ala Asp Ile Leu Val Glu Ala Leu
                85                  90                  95

Val Arg Glu Gly Val Lys Asp Val Phe Ala Tyr Pro Gly Ala Ala Ser
            100                 105                 110

Met Glu Ile His Gln Ala Leu Thr Arg Ser Lys Ile Ile Arg Asn Val
        115                 120                 125

Leu Pro Arg His Glu Gln Gly Gly Val Phe Ala Ala Glu Gly Tyr Ala
    130                 135                 140

Arg Ser Ser Gly Ile Pro Gly Val Cys Ile Ala Thr Ser Gly Pro Gly
145                 150                 155                 160

Ala Thr Asn Leu Val Ser Gly Leu Ala Asp Ala Met Leu Asp Ser Ile
                165                 170                 175
```

```
Pro Leu Val Ala Ile Thr Gly Gln Val Pro Arg Arg Met Ile Gly Thr
            180                 185                 190

Asp Ala Phe Gln Glu Thr Pro Ile Val Glu Val Thr Arg Ser Ile Thr
            195                 200                 205

Lys His Asn Tyr Leu Val Leu Asp Val Asp Ile Pro Arg Ile Val
210                 215                 220

Ser Glu Ala Phe Phe Leu Ala Ser Ser Gly Arg Pro Gly Pro Val Leu
225                 230                 235                 240

Ile Asp Val Pro Lys Asp Ile Gln Gln Leu Ala Val Pro Lys Trp
            245                 250                 255

Asn His Ser Leu Arg Leu Pro Gly Tyr Leu Ser Arg Leu Pro Lys Ala
            260                 265                 270

Pro Gly Glu Ala His Leu Glu Gln Ile Val Arg Leu Val Ser Glu Ser
            275                 280                 285

Lys Lys Pro Val Leu Tyr Val Gly Gly Gly Cys Leu Asn Ser Ser Glu
            290                 295                 300

Glu Leu Lys Arg Phe Val Glu Leu Thr Gly Ile Pro Val Ala Ser Thr
305                 310                 315                 320

Leu Met Gly Leu Gly Ala Phe Pro Ile Ser Asp Asp Leu Ser Leu Gln
            325                 330                 335

Met Leu Gly Met His Gly Thr Val Tyr Ala Asn Tyr Ala Val Asp Lys
            340                 345                 350

Ser Asp Leu Leu Leu Ala Phe Gly Val Arg Phe Asp Asp Arg Val Thr
            355                 360                 365

Gly Lys Leu Glu Ala Phe Ala Ser Arg Ala Lys Ile Val His Ile Asp
            370                 375                 380

Ile Asp Ser Ala Glu Ile Gly Lys Asn Lys Gln Pro His Val Ser Val
385                 390                 395                 400

Cys Ser Asp Val Lys Leu Ala Leu Gln Gly Ile Asn Lys Ile Leu Glu
            405                 410                 415

Thr Lys Val Ala Lys Leu Asn Leu Asp Tyr Ser Glu Trp Arg Gln Glu
            420                 425                 430

Leu Asn Glu Gln Lys Leu Lys Phe Pro Leu Ser Tyr Lys Thr Phe Gly
            435                 440                 445

Glu Ala Ile Pro Pro Gln Tyr Ala Ile Gln Val Leu Asp Glu Leu Thr
450                 455                 460

Gly Gly Asn Ala Ile Ile Ser Thr Gly Val Gly Gln His Gln Met Trp
465                 470                 475                 480

Ala Ala Gln Phe Tyr Lys Tyr Lys Lys Pro Arg Gln Trp Leu Thr Ser
            485                 490                 495

Gly Gly Leu Gly Ala Met Gly Phe Gly Leu Pro Ala Ala Ile Gly Ala
            500                 505                 510

Ala Val Ala Asn Pro Glu Ala Val Val Asp Ile Asp Gly Asp Gly
            515                 520                 525

Ser Phe Ile Met Asn Val Gln Glu Leu Ala Thr Ile Arg Val Glu Asn
530                 535                 540

Leu Pro Val Lys Ile Leu Leu Leu Asn Asn Gln His Leu Gly Met Val
545                 550                 555                 560

Val Gln Trp Glu Asp Arg Phe Tyr Lys Ala Asn Arg Ala His Thr Tyr
            565                 570                 575

Leu Gly Asp Pro Ser Asn Glu Ser Glu Ile Phe Pro Asn Met Leu Lys
            580                 585                 590

Phe Ala Glu Ala Cys Gly Ile Pro Ala Ala Arg Val Thr Lys Lys Glu
```

```
                595                 600                 605
Asp Leu Lys Ala Ala Met Gln Lys Met Leu Asp Thr Pro Gly Pro Tyr
    610                 615                 620

Leu Leu Asp Val Ile Val Pro His Gln Glu His Val Leu Pro Met Ile
625                 630                 635                 640

Pro Ser Gly Gly Ala Phe Lys Asp Val Ile Thr Glu Gly Asp Gly Arg
                645                 650                 655

Thr Gln Tyr

<210> SEQ ID NO 9
<211> LENGTH: 637
<212> TYPE: PRT
<213> ORGANISM: Brassica napus

<400> SEQUENCE: 9

Met Ala Ser Phe Ser Phe Phe Gly Thr Ile Pro Ser Ser Pro Thr Lys
1               5                   10                  15

Ala Ser Val Phe Ser Leu Pro Val Ser Val Thr Thr Leu Pro Ser Phe
                20                  25                  30

Pro Arg Arg Arg Ala Thr Arg Val Ser Val Ser Ala Asn Ser Lys Lys
            35                  40                  45

Asp Gln Asp Arg Thr Ala Ser Arg Arg Glu Asn Pro Ser Thr Phe Ser
        50                  55                  60

Ser Lys Tyr Ala Pro Asn Val Pro Arg Ser Gly Ala Asp Ile Leu Val
65                  70                  75                  80

Glu Ala Leu Glu Arg Gln Gly Val Asp Val Val Phe Ala Tyr Pro Gly
                85                  90                  95

Ala Ala Ser Met Glu Ile His Gln Ala Leu Thr Arg Ser Asn Thr Ile
                100                 105                 110

Arg Asn Val Leu Pro Arg His Glu Gln Gly Gly Ile Phe Ala Ala Glu
            115                 120                 125

Gly Tyr Ala Arg Ser Ser Gly Lys Pro Gly Ile Cys Ile Ala Thr Ser
        130                 135                 140

Gly Pro Gly Ala Met Asn Leu Val Ser Gly Leu Ala Asp Ala Leu Phe
145                 150                 155                 160

Asp Ser Val Pro Leu Ile Ala Ile Thr Gly Gln Val Pro Arg Arg Met
                165                 170                 175

Ile Gly Thr Met Ala Phe Gln Glu Thr Pro Val Val Glu Val Thr Arg
                180                 185                 190

Thr Ile Thr Lys His Asn Tyr Leu Val Met Glu Val Asp Asp Ile Pro
            195                 200                 205

Arg Ile Val Arg Glu Ala Phe Phe Leu Ala Thr Ser Val Arg Pro Gly
        210                 215                 220

Pro Val Leu Ile Asp Val Pro Lys Asp Val Gln Gln Gln Phe Ala Ile
225                 230                 235                 240

Pro Asn Trp Glu Gln Pro Met Arg Leu Pro Leu Tyr Met Ser Thr Met
                245                 250                 255

Pro Lys Pro Pro Lys Val Ser His Leu Glu Gln Ile Leu Arg Leu Val
                260                 265                 270

Ser Glu Ser Lys Arg Pro Val Leu Tyr Val Gly Gly Gly Cys Leu Asn
            275                 280                 285

Ser Ser Glu Glu Leu Arg Arg Phe Val Glu Leu Thr Gly Ile Pro Val
        290                 295                 300

Ala Ser Thr Phe Met Gly Leu Gly Ser Tyr Pro Cys Asp Asp Glu Glu
305                 310                 315                 320
```

```
Phe Ser Leu Gln Met Leu Gly Met His Gly Thr Val Tyr Ala Asn Tyr
            325                 330                 335

Ala Val Glu Tyr Ser Asp Leu Leu Ala Phe Gly Val Arg Phe Asp
        340                 345                 350

Asp Arg Val Thr Gly Lys Leu Glu Ala Phe Ala Ser Arg Ala Lys Ile
            355                 360                 365

Val His Ile Asp Ile Asp Ser Thr Glu Ile Gly Lys Asn Lys Thr Pro
370                 375                 380

His Val Ser Val Cys Cys Asp Val Gln Leu Ala Leu Gln Gly Met Asn
385                 390                 395                 400

Glu Val Leu Glu Asn Arg Arg Asp Val Leu Asp Phe Gly Glu Trp Arg
                405                 410                 415

Cys Glu Leu Asn Glu Gln Arg Leu Lys Phe Pro Leu Arg Tyr Lys Thr
                420                 425                 430

Phe Gly Glu Glu Ile Pro Pro Gln Tyr Ala Ile Gln Leu Leu Asp Glu
            435                 440                 445

Leu Thr Asp Gly Lys Ala Ile Ile Thr Thr Gly Val Gly Gln His Gln
        450                 455                 460

Met Trp Ala Ala Gln Phe Tyr Arg Phe Lys Lys Pro Arg Gln Trp Leu
465                 470                 475                 480

Ser Ser Gly Gly Leu Gly Ala Met Gly Phe Gly Leu Pro Ala Ala Met
                485                 490                 495

Gly Ala Ala Ile Ala Asn Pro Gly Ala Val Val Asp Ile Asp Gly
            500                 505                 510

Asp Gly Ser Phe Ile Met Asn Ile Gln Glu Leu Ala Thr Ile Arg Val
        515                 520                 525

Glu Asn Leu Pro Val Lys Val Leu Leu Ile Asn Asn Gln His Leu Gly
            530                 535                 540

Met Val Leu Gln Trp Glu Asp His Phe Tyr Ala Ala Asn Arg Ala Asp
545                 550                 555                 560

Ser Phe Leu Gly Asp Pro Ala Asn Pro Glu Ala Val Phe Pro Asp Met
                565                 570                 575

Leu Leu Phe Ala Ala Ser Cys Gly Ile Pro Ala Ala Arg Val Thr Arg
            580                 585                 590

Arg Glu Asp Leu Arg Glu Ala Ile Gln Thr Met Leu Asp Thr Pro Gly
        595                 600                 605

Pro Phe Leu Leu Asp Val Val Cys Pro His Gln Asp His Val Leu Pro
610                 615                 620

Leu Ile Pro Ser Gly Gly Thr Phe Lys Asp Ile Ile Val
625                 630                 635

<210> SEQ ID NO 10
<211> LENGTH: 599
<212> TYPE: PRT
<213> ORGANISM: Brassica napus

<400> SEQUENCE: 10

Met Ser His Leu Leu Pro Leu Lys Lys Pro Thr Arg Thr Arg Leu Ser
1               5                   10                  15

Ser Pro Ala Thr Leu Pro Asp Glu Pro Arg Lys Gly Ala Asp Ile Leu
            20                  25                  30

Val Glu Ala Leu Glu Arg Gln Gly Val Glu Thr Val Phe Ala Tyr Pro
        35                  40                  45

Gly Ala Ala Ser Met Glu Ile His Gln Ala Leu Thr Arg Ser Ser Thr
    50                  55                  60
```

```
Ile Arg Asn Val Leu Pro Arg His Glu Gln Gly Gly Val Phe Ala Ala
 65                  70                  75                  80

Glu Gly Tyr Ala Arg Ser Ser Gly Lys Pro Gly Ile Cys Ile Ala Thr
                 85                  90                  95

Ser Gly Pro Gly Ala Thr Asn Leu Val Ser Gly Leu Ala Asp Ala Met
            100                 105                 110

Leu Asp Ser Val Pro Leu Val Ala Ile Thr Gly Gln Val Pro Arg Arg
        115                 120                 125

Met Ile Gly Thr Asp Ala Phe Gln Glu Thr Pro Ile Val Glu Val Thr
    130                 135                 140

Arg Ser Ile Thr Lys His Asn Tyr Leu Val Met Asp Val Asp Asp Ile
145                 150                 155                 160

Pro Arg Ile Val Gln Glu Ala Phe Phe Leu Ala Thr Ser Gly Arg Pro
                165                 170                 175

Gly Pro Val Leu Val Asp Val Pro Lys Asp Ile Gln Gln Gln Leu Ala
            180                 185                 190

Ile Pro Asn Trp Asp Gln Pro Met Arg Leu Pro Gly Tyr Met Ser Arg
        195                 200                 205

Leu Pro Gln Pro Pro Glu Val Ser Gln Leu Gly Gln Ile Val Arg Leu
    210                 215                 220

Ile Ser Glu Ser Lys Arg Pro Val Leu Tyr Val Gly Gly Gly Ser Leu
225                 230                 235                 240

Asn Ser Ser Glu Glu Leu Gly Arg Phe Val Glu Leu Thr Gly Ile Pro
                245                 250                 255

Val Ala Ser Thr Leu Met Gly Leu Gly Ser Tyr Pro Cys Asn Asp Glu
            260                 265                 270

Leu Ser Leu Gln Met Leu Gly Met His Gly Thr Val Tyr Ala Asn Tyr
        275                 280                 285

Ala Val Glu His Ser Asp Leu Leu Leu Ala Phe Gly Val Arg Phe Asp
    290                 295                 300

Asp Arg Val Thr Gly Lys Leu Glu Ala Phe Ala Ser Arg Ala Lys Ile
305                 310                 315                 320

Val His Ile Asp Ile Asp Ser Ala Glu Ile Gly Lys Asn Lys Thr Pro
                325                 330                 335

His Val Ser Val Cys Gly Asp Val Lys Leu Ala Leu Gln Gly Met Asn
            340                 345                 350

Lys Val Leu Glu Asn Arg Ala Glu Glu Leu Lys Leu Asp Phe Gly Val
        355                 360                 365

Trp Arg Ser Glu Leu Ser Glu Gln Lys Gln Lys Phe Pro Leu Ser Phe
    370                 375                 380

Lys Thr Phe Gly Glu Ala Ile Pro Pro Gln Tyr Ala Ile Gln Ile Leu
385                 390                 395                 400

Asp Glu Leu Thr Glu Gly Lys Ala Ile Ile Ser Thr Gly Val Gly Gln
                405                 410                 415

His Gln Met Trp Ala Ala Gln Phe Tyr Lys Tyr Arg Lys Pro Arg Gln
            420                 425                 430

Trp Leu Ser Ser Ser Gly Leu Gly Ala Met Gly Phe Gly Leu Pro Ala
        435                 440                 445

Ala Ile Gly Ala Ser Val Ala Asn Pro Asp Ala Ile Val Val Asp Ile
    450                 455                 460

Asp Gly Asp Gly Ser Phe Ile Met Asn Val Gln Glu Leu Ala Thr Ile
465                 470                 475                 480

Arg Val Glu Asn Leu Pro Val Lys Ile Leu Leu Leu Asn Asn Gln His
```

-continued

```
                     485                 490                 495
Leu Gly Met Val Met Gln Trp Glu Asp Arg Phe Tyr Lys Ala Asn Arg
                500                 505                 510

Ala His Thr Tyr Leu Gly Asp Pro Ala Arg Glu Asn Glu Ile Phe Pro
            515                 520                 525

Asn Met Leu Gln Phe Ala Gly Ala Cys Gly Ile Pro Ala Ala Arg Val
        530                 535                 540

Thr Lys Lys Glu Glu Leu Arg Glu Ala Ile Gln Thr Met Leu Asp Thr
545                 550                 555                 560

Pro Gly Pro Tyr Leu Leu Asp Val Ile Cys Pro His Gln Glu His Val
                565                 570                 575

Leu Pro Met Ile Pro Ser Gly Gly Thr Phe Lys Asp Val Ile Thr Glu
            580                 585                 590

Gly Asp Gly Arg Thr Lys Tyr
            595

<210> SEQ ID NO 11
<211> LENGTH: 667
<212> TYPE: PRT
<213> ORGANISM: Nicotiana tabacum

<400> SEQUENCE: 11

Met Ala Ala Ala Pro Ser Pro Ser Ser Ala Phe Ser Lys Thr
1               5                   10                  15

Leu Ser Pro Ser Ser Thr Ser Ser Thr Leu Leu Pro Arg Ser Thr
            20                  25                  30

Phe Pro Phe Pro His His Pro His Lys Thr Thr Pro Pro Leu His
        35                  40                  45

Leu Thr His Thr His Ile His Ile His Ser Gln Arg Arg Phe Thr
    50                  55                  60

Ile Ser Asn Val Ile Ser Thr Asn Gln Lys Val Ser Gln Thr Glu Lys
65                  70                  75                  80

Thr Glu Thr Phe Val Ser Arg Phe Ala Pro Asp Pro Arg Lys Gly
                85                  90                  95

Ser Asp Val Leu Val Glu Ala Leu Glu Arg Glu Gly Val Thr Asp Val
            100                 105                 110

Phe Ala Tyr Pro Gly Ala Ala Ser Met Glu Ile His Gln Ala Leu Thr
        115                 120                 125

Arg Ser Ser Ile Ile Arg Asn Val Leu Pro Arg His Glu Gln Gly Gly
    130                 135                 140

Val Phe Ala Ala Glu Gly Tyr Ala Arg Ala Thr Gly Phe Pro Gly Val
145                 150                 155                 160

Cys Ile Ala Thr Ser Gly Pro Gly Ala Thr Asn Leu Val Ser Gly Leu
                165                 170                 175

Ala Asp Ala Leu Leu Asp Ser Val Pro Ile Val Ala Ile Thr Gly Gln
            180                 185                 190

Val Pro Arg Arg Met Ile Gly Thr Asp Ala Phe Gln Glu Thr Pro Ile
        195                 200                 205

Val Glu Val Thr Arg Ser Ile Thr Lys His Asn Tyr Leu Val Met Asp
    210                 215                 220

Val Glu Asp Ile Pro Arg Val Arg Glu Ala Phe Phe Leu Ala Arg
225                 230                 235                 240

Ser Gly Arg Pro Gly Pro Ile Leu Ile Asp Val Pro Lys Asp Ile Gln
                245                 250                 255

Gln Gln Leu Val Ile Pro Asp Trp Asp Gln Pro Met Arg Leu Pro Gly
```

```
                        260                 265                 270
Tyr Met Ser Arg Leu Pro Lys Leu Pro Asn Glu Met Leu Leu Glu Gln
                275                 280                 285

Ile Val Arg Leu Ile Ser Glu Ser Lys Lys Pro Val Leu Tyr Val Gly
            290                 295                 300

Gly Gly Cys Ser Gln Ser Ser Glu Asp Leu Arg Arg Phe Val Glu Leu
305                 310                 315                 320

Thr Gly Ile Pro Val Ala Ser Thr Leu Met Gly Leu Gly Ala Phe Pro
                325                 330                 335

Thr Gly Asp Glu Leu Ser Leu Ser Met Leu Gly Met His Gly Thr Val
                340                 345                 350

Tyr Ala Asn Tyr Ala Val Asp Ser Ser Asp Leu Leu Leu Ala Phe Gly
                355                 360                 365

Val Arg Phe Asp Asp Arg Val Thr Gly Lys Leu Glu Ala Phe Ala Ser
            370                 375                 380

Arg Ala Lys Ile Val His Ile Asp Ile Asp Ser Ala Glu Ile Gly Lys
385                 390                 395                 400

Asn Lys Gln Pro His Val Ser Ile Cys Ala Asp Ile Lys Leu Ala Leu
                405                 410                 415

Gln Gly Leu Asn Ser Ile Leu Glu Ser Lys Glu Gly Lys Leu Lys Leu
                420                 425                 430

Asp Phe Ser Ala Trp Arg Gln Glu Leu Thr Glu Gln Lys Val Lys His
            435                 440                 445

Pro Leu Asn Phe Lys Thr Phe Gly Asp Ala Ile Pro Pro Gln Tyr Ala
            450                 455                 460

Ile Gln Val Leu Asp Glu Leu Thr Asn Gly Asn Ala Ile Ile Ser Thr
465                 470                 475                 480

Gly Val Gly Gln His Gln Met Trp Ala Ala Gln Tyr Tyr Lys Tyr Arg
                485                 490                 495

Lys Pro Arg Gln Trp Leu Thr Ser Gly Gly Leu Gly Ala Met Gly Phe
                500                 505                 510

Gly Leu Pro Ala Ala Ile Gly Ala Ala Val Gly Arg Pro Asp Glu Val
            515                 520                 525

Val Val Asp Ile Asp Gly Asp Gly Ser Phe Ile Met Asn Val Gln Glu
            530                 535                 540

Leu Ala Thr Ile Lys Val Glu Asn Leu Pro Val Lys Ile Met Leu Leu
545                 550                 555                 560

Asn Asn Gln His Leu Gly Met Val Val Gln Trp Glu Asp Arg Phe Tyr
                565                 570                 575

Lys Ala Asn Arg Ala His Thr Tyr Leu Gly Asn Pro Ser Asn Glu Ala
                580                 585                 590

Glu Ile Phe Pro Asn Met Leu Lys Phe Ala Glu Ala Cys Gly Val Pro
            595                 600                 605

Ala Ala Arg Val Thr His Arg Asp Asp Leu Arg Ala Ala Ile Gln Lys
            610                 615                 620

Met Leu Asp Thr Pro Gly Pro Tyr Leu Leu Asp Val Ile Val Pro His
625                 630                 635                 640

Gln Glu His Val Leu Pro Met Ile Pro Ser Gly Gly Ala Phe Lys Asp
                645                 650                 655

Val Ile Thr Glu Gly Asp Gly Arg Ser Ser Tyr
                660                 665

<210> SEQ ID NO 12
<211> LENGTH: 664
```

<212> TYPE: PRT
<213> ORGANISM: Nicotiana tabacum

<400> SEQUENCE: 12

```
Met Ala Ala Ala Ala Ala Pro Ser Pro Ser Phe Ser Lys Thr Leu
1               5                   10                  15

Ser Ser Ser Ser Ser Lys Ser Ser Thr Leu Leu Pro Arg Ser Thr Phe
            20                  25                  30

Pro Phe Pro His His Pro His Lys Thr Thr Pro Pro Leu His Leu
        35                  40                  45

Thr Pro Thr His Ile His Ser Gln Arg Arg Phe Thr Ile Ser Asn
50                  55                  60

Val Ile Ser Thr Thr Gln Lys Val Ser Glu Thr Gln Lys Ala Glu Thr
65                  70                  75                  80

Phe Val Ser Arg Phe Ala Pro Asp Glu Pro Arg Lys Gly Ser Asp Val
                85                  90                  95

Leu Val Glu Ala Leu Glu Arg Glu Gly Val Thr Asp Val Phe Ala Tyr
            100                 105                 110

Pro Gly Ala Ala Ser Met Glu Ile His Gln Ala Leu Thr Arg Ser Ser
        115                 120                 125

Ile Ile Arg Asn Val Leu Pro Arg His Glu Gln Gly Gly Val Phe Ala
130                 135                 140

Ala Glu Gly Tyr Ala Arg Ala Thr Gly Phe Pro Gly Val Cys Ile Ala
145                 150                 155                 160

Thr Ser Gly Pro Gly Ala Thr Asn Leu Val Ser Gly Leu Ala Asp Ala
                165                 170                 175

Leu Leu Asp Ser Val Pro Ile Val Ala Ile Thr Gly Gln Val Pro Arg
            180                 185                 190

Arg Met Ile Gly Thr Asp Ala Phe Gln Glu Thr Pro Ile Val Glu Val
        195                 200                 205

Thr Arg Ser Ile Thr Lys His Asn Tyr Leu Val Met Asp Val Glu Asp
210                 215                 220

Ile Pro Arg Val Val Arg Glu Ala Phe Phe Leu Ala Arg Ser Gly Arg
225                 230                 235                 240

Pro Gly Pro Val Leu Ile Asp Val Pro Lys Asp Ile Gln Gln Gln Leu
                245                 250                 255

Val Ile Pro Asp Trp Asp Gln Pro Met Arg Leu Pro Gly Tyr Met Ser
            260                 265                 270

Arg Leu Pro Lys Leu Pro Asn Glu Met Leu Leu Glu Gln Ile Val Arg
        275                 280                 285

Leu Ile Ser Glu Ser Lys Lys Pro Val Leu Tyr Val Gly Gly Gly Cys
290                 295                 300

Ser Gln Ser Ser Glu Glu Leu Arg Arg Phe Val Glu Leu Thr Gly Ile
305                 310                 315                 320

Pro Val Ala Ser Thr Leu Met Gly Leu Gly Ala Phe Pro Thr Gly Asp
                325                 330                 335

Glu Leu Ser Leu Ser Met Leu Gly Met His Gly Thr Val Tyr Ala Asn
            340                 345                 350

Tyr Ala Val Asp Ser Ser Asp Leu Leu Leu Ala Phe Gly Val Arg Phe
        355                 360                 365

Asp Asp Arg Val Thr Gly Lys Leu Glu Ala Phe Ala Ser Arg Ala Lys
370                 375                 380

Ile Val His Ile Asp Ile Asp Ser Ala Glu Ile Gly Lys Asn Lys Gln
385                 390                 395                 400
```

```
Pro His Val Ser Ile Cys Ala Asp Ile Lys Leu Ala Leu Gln Gly Leu
                405                 410                 415

Asn Ser Ile Leu Glu Ser Lys Glu Gly Lys Leu Lys Leu Asp Phe Ser
            420                 425                 430

Ala Trp Arg Gln Glu Leu Thr Val Gln Lys Val Lys Tyr Pro Leu Asn
        435                 440                 445

Phe Lys Thr Phe Gly Asp Ala Ile Pro Pro Gln Tyr Ala Ile Gln Val
    450                 455                 460

Leu Asp Glu Leu Thr Asn Gly Ser Ala Ile Ile Ser Thr Gly Val Gly
465                 470                 475                 480

Gln His Gln Met Trp Ala Ala Gln Tyr Tyr Lys Tyr Arg Lys Pro Arg
                485                 490                 495

Gln Trp Leu Thr Ser Gly Gly Leu Gly Ala Met Gly Phe Gly Leu Pro
            500                 505                 510

Ala Ala Ile Gly Ala Ala Val Gly Arg Pro Asp Glu Val Val Val Asp
        515                 520                 525

Ile Asp Gly Asp Gly Ser Phe Ile Met Asn Val Gln Glu Leu Ala Thr
    530                 535                 540

Ile Lys Val Glu Asn Leu Pro Val Lys Ile Met Leu Leu Asn Asn Gln
545                 550                 555                 560

His Leu Gly Met Val Val Gln Trp Glu Asp Arg Phe Tyr Lys Ala Asn
                565                 570                 575

Arg Ala His Thr Tyr Leu Gly Asn Pro Ser Asn Glu Ala Glu Ile Phe
            580                 585                 590

Pro Asn Met Leu Lys Phe Ala Glu Ala Cys Gly Val Pro Ala Ala Arg
        595                 600                 605

Val Thr His Arg Asp Asp Leu Arg Ala Ala Ile Gln Lys Met Leu Asp
    610                 615                 620

Thr Pro Gly Pro Tyr Leu Leu Asp Val Ile Val Pro His Gln Glu His
625                 630                 635                 640

Val Leu Pro Met Ile Pro Ser Gly Gly Ala Phe Lys Asp Val Ile Thr
                645                 650                 655

Glu Gly Asp Gly Arg Ser Ser Tyr
            660

<210> SEQ ID NO 13
<211> LENGTH: 640
<212> TYPE: PRT
<213> ORGANISM: Lolium multiflorum

<400> SEQUENCE: 13

Met Ala Thr Ala Thr Ser Thr Ala Val Ala Phe Ser Gly Ala Thr Ala
1               5                   10                  15

Thr Leu Pro Lys Pro Arg Thr Leu Pro Arg His Leu Leu Pro Ser Ser
            20                  25                  30

Arg Arg Ala Leu Ala Ala Pro Ile Arg Cys Ser Ala Val Ser Pro Ser
        35                  40                  45

Pro Ser Pro Ala Pro Pro Ala Thr Ala Leu Arg Pro Trp Gly Pro Ser
    50                  55                  60

Glu Pro Arg Lys Gly Ala Asp Ile Leu Val Glu Ala Leu Glu Arg Cys
65                  70                  75                  80

Gly Ile Ser Asp Val Phe Ala Tyr Pro Gly Ala Ala Ser Met Glu Ile
                85                  90                  95

His Gln Ala Leu Thr Ser Ser Pro Leu Ile Thr Asn His Leu Phe Arg
            100                 105                 110
```

-continued

His Glu Gln Gly Glu Ala Phe Ala Ala Ser Gly Tyr Ala Arg Ala Ser
    115                 120                 125

Gly Arg Val Gly Val Cys Val Ala Thr Ser Gly Pro Gly Ala Thr Asn
130                 135                 140

Leu Val Ser Ala Leu Ala Asp Ala Leu Leu Asp Ser Ile Pro Met Val
145                 150                 155                 160

Ala Ile Thr Gly Gln Val Pro Arg Arg Met Ile Gly Thr Asp Ala Phe
                165                 170                 175

Gln Glu Thr Pro Ile Val Glu Val Thr Arg Ser Ile Thr Lys His Asn
            180                 185                 190

Tyr Leu Val Leu Asp Val Glu Asp Ile Pro Arg Val Ile Gln Glu Ala
        195                 200                 205

Phe Phe Leu Ala Ser Ser Gly Arg Pro Gly Pro Val Leu Val Asp Ile
    210                 215                 220

Pro Lys Asp Ile Gln Gln Met Ala Val Pro Val Trp Asp Ala Pro
225                 230                 235                 240

Met Ser Leu Pro Gly Tyr Ile Ala Arg Leu Pro Lys Pro Pro Ala Thr
                245                 250                 255

Glu Leu Leu Glu Gln Val Leu Arg Leu Val Gly Glu Glu Arg Arg Pro
            260                 265                 270

Ile Leu Tyr Val Gly Gly Gly Cys Ser Ala Ser Gly Glu Asp Val Arg
        275                 280                 285

Arg Phe Val Glu Leu Thr Gly Ile Pro Val Thr Thr Thr Leu Met Gly
    290                 295                 300

Leu Gly Asn Phe Pro Ser Asp Asp Pro Leu Ser Leu Arg Met Leu Gly
305                 310                 315                 320

Met His Gly Thr Val Tyr Ala Asn Tyr Ala Val Asp Lys Ala Asp Leu
                325                 330                 335

Leu Leu Ala Phe Gly Val Arg Phe Asp Asp Arg Val Thr Gly Lys Ile
            340                 345                 350

Glu Ala Phe Ala Ser Arg Ser Lys Ile Val His Ile Asp Ile Asp Pro
        355                 360                 365

Ala Glu Ile Gly Lys Asn Lys Gln Pro His Val Ser Ile Cys Ala Asp
    370                 375                 380

Val Lys Leu Ala Leu Gln Gly Leu Asn Ala Val Leu Thr Gly Ser Lys
385                 390                 395                 400

Cys Asp Lys Ser Phe Asp Phe Ala Ser Trp His Asp Glu Leu Glu Gln
                405                 410                 415

Gln Lys Arg Glu Phe Pro Leu Gly Tyr Lys Thr Phe Gly Glu Ala Ile
            420                 425                 430

Pro Pro Gln Tyr Ala Ile Gln Val Leu Asp Glu Leu Thr Lys Gly Glu
        435                 440                 445

Ala Ile Ile Ala Thr Gly Val Gly Gln His Gln Met Trp Ala Ala Gln
    450                 455                 460

Tyr Tyr Thr Tyr Lys Arg Pro Arg Gln Val Leu Ser Ser Ala Gly Leu
465                 470                 475                 480

Gly Ala Met Gly Phe Gly Leu Pro Ala Ala Gly Thr Ala Val Ala
                485                 490                 495

Asn Pro Gly Val Thr Val Val Asp Ile Asp Gly Asp Gly Ser Phe Leu
            500                 505                 510

Met Asn Ile Gln Glu Leu Ala Leu Ile Arg Ile Glu Asn Leu Pro Val
        515                 520                 525

Lys Val Met Ile Leu Asn Asn Gln His Leu Gly Met Val Val Gln Trp
    530                 535                 540

```
Glu Asp Arg Phe Tyr Lys Ala Asn Arg Ala His Thr Tyr Leu Gly Asn
545                 550                 555                 560

Pro Glu Asn Glu Ser Glu Ile Tyr Pro Asp Phe Val Thr Ile Ala Lys
                565                 570                 575

Gly Phe Asn Val Pro Ala Val Arg Val Thr Lys Arg Ser Glu Val Arg
                580                 585                 590

Ala Ala Ile Lys Lys Met Leu Glu Thr Pro Gly Pro Tyr Leu Leu Asp
                595                 600                 605

Ile Ile Val Pro His Gln Glu His Val Leu Pro Met Ile Pro Ser Gly
            610                 615                 620

Gly Ala Phe Lys Asp Ile Ile Met Glu Gly Asp Gly Arg Ile Ser Tyr
625                 630                 635                 640

<210> SEQ ID NO 14
<211> LENGTH: 670
<212> TYPE: PRT
<213> ORGANISM: Arabidopsis thaliana

<400> SEQUENCE: 14

Met Ala Ala Thr Thr Thr Thr Thr Ser Ser Ser Ile Ser Phe
1               5                   10                  15

Ser Thr Lys Pro Ser Pro Ser Ser Lys Ser Pro Leu Pro Ile Ser
            20                  25                  30

Arg Phe Ser Leu Pro Phe Ser Leu Asn Pro Asn Lys Ser Ser Ser Ser
            35                  40                  45

Ser Arg Arg Arg Gly Ile Lys Ser Ser Ser Pro Ser Ile Ser Ala
50                  55                  60

Val Leu Asn Thr Thr Thr Asn Val Thr Thr Pro Ser Pro Thr Lys
65                  70                  75                  80

Pro Thr Lys Pro Glu Thr Phe Ile Ser Arg Phe Ala Pro Asp Gln Pro
                85                  90                  95

Arg Lys Gly Ala Asp Ile Leu Val Glu Ala Leu Glu Arg Gln Gly Val
                100                 105                 110

Glu Thr Val Phe Ala Tyr Pro Gly Ala Ala Ser Met Glu Ile His Gln
                115                 120                 125

Ala Leu Thr Arg Ser Ser Ser Ile Arg Asn Val Leu Pro Arg His Glu
                130                 135                 140

Gln Gly Gly Val Phe Ala Ala Glu Gly Tyr Ala Arg Ser Ser Gly Lys
145                 150                 155                 160

Pro Gly Ile Cys Ile Ala Thr Ser Gly Pro Gly Ala Thr Asn Leu Val
                165                 170                 175

Ser Gly Leu Ala Asp Ala Leu Leu Asp Ser Val Pro Leu Val Ala Ile
                180                 185                 190

Thr Gly Gln Val Pro Arg Arg Met Ile Gly Thr Asp Ala Phe Gln Glu
                195                 200                 205

Thr Pro Ile Val Glu Val Thr Arg Ser Ile Thr Lys His Asn Tyr Leu
                210                 215                 220

Val Met Asp Val Glu Asp Ile Pro Arg Ile Ile Glu Glu Ala Phe Phe
225                 230                 235                 240

Leu Ala Thr Ser Gly Arg Pro Gly Pro Val Leu Val Asp Val Pro Lys
                245                 250                 255

Asp Ile Gln Gln Gln Leu Ala Ile Pro Asn Trp Glu Gln Ala Met Arg
                260                 265                 270

Leu Pro Gly Tyr Met Ser Arg Met Pro Lys Pro Pro Glu Asp Ser His
                275                 280                 285
```

Leu Glu Gln Ile Val Arg Leu Ile Ser Glu Ser Lys Lys Pro Val Leu
        290                 295                 300

Tyr Val Gly Gly Cys Leu Asn Ser Ser Asp Glu Leu Gly Arg Phe
305                 310                 315                 320

Val Glu Leu Thr Gly Ile Pro Val Ala Ser Thr Leu Met Gly Leu Gly
                325                 330                 335

Ser Tyr Pro Cys Asp Asp Glu Leu Ser Leu His Met Leu Gly Met His
                340                 345                 350

Gly Thr Val Tyr Ala Asn Tyr Ala Val Glu His Ser Asp Leu Leu Leu
                355                 360                 365

Ala Phe Gly Val Arg Phe Asp Asp Arg Val Thr Gly Lys Leu Glu Ala
370                 375                 380

Phe Ala Ser Arg Ala Lys Ile Val His Ile Asp Ile Asp Ser Ala Glu
385                 390                 395                 400

Ile Gly Lys Asn Lys Thr Pro His Val Ser Val Cys Gly Asp Val Lys
                405                 410                 415

Leu Ala Leu Gln Gly Met Asn Lys Val Leu Glu Asn Arg Ala Glu Glu
                420                 425                 430

Leu Lys Leu Asp Phe Gly Val Trp Arg Asn Glu Leu Asn Val Gln Lys
        435                 440                 445

Gln Lys Phe Pro Leu Ser Phe Lys Thr Phe Gly Glu Ala Ile Pro Pro
450                 455                 460

Gln Tyr Ala Ile Lys Val Leu Asp Glu Leu Thr Asp Gly Lys Ala Ile
465                 470                 475                 480

Ile Ser Thr Gly Val Gly Gln His Gln Met Trp Ala Ala Gln Phe Tyr
                485                 490                 495

Asn Tyr Lys Lys Pro Arg Gln Trp Leu Ser Ser Gly Gly Leu Gly Ala
                500                 505                 510

Met Gly Phe Gly Leu Pro Ala Ala Ile Gly Ala Ser Val Ala Asn Pro
        515                 520                 525

Asp Ala Ile Val Val Asp Ile Asp Gly Asp Gly Ser Phe Ile Met Asn
530                 535                 540

Val Gln Glu Leu Ala Thr Ile Arg Val Glu Asn Leu Pro Val Lys Val
545                 550                 555                 560

Leu Leu Leu Asn Asn Gln His Leu Gly Met Val Met Gln Trp Glu Asp
                565                 570                 575

Arg Phe Tyr Lys Ala Asn Arg Ala His Thr Phe Leu Gly Asp Pro Ala
                580                 585                 590

Gln Glu Asp Glu Ile Phe Pro Asn Met Leu Leu Phe Ala Ala Ala Cys
        595                 600                 605

Gly Ile Pro Ala Ala Arg Val Thr Lys Lys Ala Asp Leu Arg Glu Ala
610                 615                 620

Ile Gln Thr Met Leu Asp Thr Pro Gly Pro Tyr Leu Leu Asp Val Ile
625                 630                 635                 640

Cys Pro His Gln Glu His Val Leu Pro Met Ile Pro Ser Gly Gly Thr
                645                 650                 655

Phe Asn Asp Val Ile Thr Glu Gly Asp Gly Arg Ile Lys Tyr
                660                 665                 670

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: synthetic -continued

```
      DNA

<400> SEQUENCE: 15
ccaccaccca ccatggctac g                                               21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 16
gaagaggtgg ttggtgatga                                                 20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 17
gcaaccaacc tcgtgtccgc                                                 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 18
gaaggcttcc tgtatgacgc                                                 20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 19
gaattgcgct ggtttgttga                                                 20

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 20
ctcaattttc cctgtcacac g                                               21

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: synthetic
      DNA
```

```
<400> SEQUENCE: 21
ggtagcttcc tcatgaacat                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 22
aatgttcatg aggaagctac                                              20

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 23
cattcaggtc aaacataggc c                                            21

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: synthetic
      DNA
<220> FEATURE:
<221> NAME/KEY: misc_feature
<222> LOCATION: (10)..(12)
<223> OTHER INFORMATION: n is a, c, g, or t

<400> SEQUENCE: 24
tacccgggcn nngcgtccat ggagatcca                                    29

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 25
tgtgcttggt gatgga                                                  16

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 26
gggctggcaa gccacgtttg gtg                                          23

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: synthetic
```

-continued
           DNA

<400> SEQUENCE: 27
cagcgacgtg ttcgccta                                                    18

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 28
ccccagccgc atgatcggca ccgacgcctt                                       30

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 29
ctgggacacc tcgatgaat                                                   19

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 30
aactgggata ccagtcagct c                                                21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 31
gctctgctac aacagagcac a                                                21

<210> SEQ ID NO 32
<211> LENGTH: 17
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 32
gattgcctca cctttcg                                                     17

<210> SEQ ID NO 33
<211> LENGTH: 17
<212> TYPE: DNA
<213> ORGANISM: Artificial Sequence
<220> FEATURE:
<223> OTHER INFORMATION: Description of Artificial Sequence: synthetic
      DNA

```
<400> SEQUENCE: 33
cagcccaaat cccattg                                                      17

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 34
aggtgtcaca gttgttg                                                      17

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 35
tcaaggacat gatcctggat gg                                                22

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 36
agtcctgcca tcaccatcca g                                                 21

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 37
ccgggagctg catgtgtcag agg                                               23

<210> SEQ ID NO 38
<211> LENGTH: 1935
<212> TYPE: DNA
<213> ORGANISM: Oryza sativa
<220> FEATURE:
<221> NAME/KEY: CDS
<222> LOCATION: (1)..(1935)

<400> SEQUENCE: 38 atg gct acg acc gcc gcg gcc gcg gcc gcc gcc ctg tcc gcc gcc gcg        48
Met Ala Thr Thr Ala Ala Ala Ala Ala Ala Ala Leu Ser Ala Ala Ala
1               5                   10                  15 acg gcc aag acc ggc cgt aag aac cac cag cga cac cac gtc ctt ccc        96
Thr Ala Lys Thr Gly Arg Lys Asn His Gln Arg His His Val Leu Pro
            20                  25                  30 gct cga ggc cgg gtg ggg gcg gcg gcg gtc agg tgc tcg gcg gtg tcc       144
Ala Arg Gly Arg Val Gly Ala Ala Ala Val Arg Cys Ser Ala Val Ser
        35                  40                  45 ccg gtc acc ccg ccg tcc ccg gcg ccg ccg gcc acg ccg ctc cgg ccg       192
```

-continued

```
               Pro Val Thr Pro Pro Ser Pro Ala Pro Pro Ala Thr Pro Leu Arg Pro
                   50                  55                  60 tgg ggg ccg gcc gag ccc cgc aag ggc gcg gac atc ctc gtg gag gcg         240
Trp Gly Pro Ala Glu Pro Arg Lys Gly Ala Asp Ile Leu Val Glu Ala
 65                  70                  75                  80 ctg gag cgg tgc ggc gtc agc gac gtg ttc gcc tac ccg ggc ggc gcg         288
Leu Glu Arg Cys Gly Val Ser Asp Val Phe Ala Tyr Pro Gly Gly Ala
                 85                  90                  95 tcc atg gag atc cac cag gcg ctg acg cgc tcc ccg gtc atc acc aac         336
Ser Met Glu Ile His Gln Ala Leu Thr Arg Ser Pro Val Ile Thr Asn
                100                 105                 110 cac ctc ttc cgc cac gag cag ggc gag gcg ttc gcg gcg tcc ggg tac         384
His Leu Phe Arg His Glu Gln Gly Glu Ala Phe Ala Ala Ser Gly Tyr
                115                 120                 125 gcg cgc gcg tcc ggc cgc gtc ggg gtc tgc gtc gcc acc tcc ggc ccc         432
Ala Arg Ala Ser Gly Arg Val Gly Val Cys Val Ala Thr Ser Gly Pro
            130                 135                 140 ggg gca acc aac ctc gtg tcc gcg ctc gcc gac gcg ctg ctc gac tcc         480
Gly Ala Thr Asn Leu Val Ser Ala Leu Ala Asp Ala Leu Leu Asp Ser
145                 150                 155                 160 gtc ccg atg gtc gcc atc acg ggc cag gtc ccc cgc cgc atg atc ggc         528
Val Pro Met Val Ala Ile Thr Gly Gln Val Pro Arg Arg Met Ile Gly
                165                 170                 175 acc gac gcc ttc cag gag acg ccc ata gtc gag gtc acc cgc tcc atc         576
Thr Asp Ala Phe Gln Glu Thr Pro Ile Val Glu Val Thr Arg Ser Ile
                180                 185                 190 acc aag cac aat tac ctt gtc ctt gat gtg gag gac atc ccc cgc gtc         624
Thr Lys His Asn Tyr Leu Val Leu Asp Val Glu Asp Ile Pro Arg Val
                195                 200                 205 ata cag gaa gcc ttc ttc ctc gcg tcc tcg ggc cgt cct ggc ccg gtg         672
Ile Gln Glu Ala Phe Phe Leu Ala Ser Ser Gly Arg Pro Gly Pro Val
            210                 215                 220 ctg gtc gac atc ccc aag gac atc cag cag cag atg gcc gtg ccg gtc         720
Leu Val Asp Ile Pro Lys Asp Ile Gln Gln Gln Met Ala Val Pro Val
225                 230                 235                 240 tgg gac acc tcg atg aat cta cca ggg tac atc gca cgc ctg ccc aag         768
Trp Asp Thr Ser Met Asn Leu Pro Gly Tyr Ile Ala Arg Leu Pro Lys
                245                 250                 255 cca ccc gcg aca gaa ttg ctt gag cag gtc ttg cgt ctg gtt ggc gag         816
Pro Pro Ala Thr Glu Leu Leu Glu Gln Val Leu Arg Leu Val Gly Glu
                260                 265                 270 tca cgg cgc ccg att ctc tat gtc ggt ggt ggc tgc tct gca tct ggt         864
Ser Arg Arg Pro Ile Leu Tyr Val Gly Gly Gly Cys Ser Ala Ser Gly
            275                 280                 285 gac gaa ttg cgc tgg ttt gtt gag ctg act ggt atc cca gtt aca acc         912
Asp Glu Leu Arg Trp Phe Val Glu Leu Thr Gly Ile Pro Val Thr Thr
            290                 295                 300 act ctg atg ggc ctc ggc aat ttc ccc agt gac gac ccg ttg tcc ctg         960
Thr Leu Met Gly Leu Gly Asn Phe Pro Ser Asp Asp Pro Leu Ser Leu
305                 310                 315                 320 cgc atg ctt ggg atg cat ggc acg gtg tac gca aat tat gcc gtg gat        1008
Arg Met Leu Gly Met His Gly Thr Val Tyr Ala Asn Tyr Ala Val Asp
                325                 330                 335 aag gct gac ctg ttg ctt gcg ttt ggt gtg cgg ttt gat gat cgt gtg        1056
Lys Ala Asp Leu Leu Leu Ala Phe Gly Val Arg Phe Asp Asp Arg Val
                340                 345                 350 aca ggg aaa att gag gct ttt gca agc agg gcc aag att gtg cac att        1104
Thr Gly Lys Ile Glu Ala Phe Ala Ser Arg Ala Lys Ile Val His Ile
            355                 360                 365 gac att gat cca gca gag att gga aag aac aag caa cca cat gtg tca        1152
```

```
                Asp Ile Asp Pro Ala Glu Ile Gly Lys Asn Lys Gln Pro His Val Ser
                    370                 375                 380 att tgc gca gat gtt aag ctt gct tta cag ggc ttg aat gct ctg cta            1200
Ile Cys Ala Asp Val Lys Leu Ala Leu Gln Gly Leu Asn Ala Leu Leu
385                 390                 395                 400 caa cag agc aca aca aag aca agt tct gat ttt agt gca tgg cac aat            1248
Gln Gln Ser Thr Thr Lys Thr Ser Ser Asp Phe Ser Ala Trp His Asn
                405                 410                 415 gag ttg gac cag cag aag agg gag ttt cct ctg ggg tac aaa act ttt            1296
Glu Leu Asp Gln Gln Lys Arg Glu Phe Pro Leu Gly Tyr Lys Thr Phe
            420                 425                 430 ggt gaa gag atc cca ccg caa tat gcc att cag gtg ctg gat gag ctg            1344
Gly Glu Glu Ile Pro Pro Gln Tyr Ala Ile Gln Val Leu Asp Glu Leu
        435                 440                 445 acg aaa ggt gag gca atc atc gct act ggt gtt ggg cag cac cag atg            1392
Thr Lys Gly Glu Ala Ile Ile Ala Thr Gly Val Gly Gln His Gln Met
    450                 455                 460 tgg gcg gca caa tat tac acc tac aag cgg cca cgg cag tgg ctg tct            1440
Trp Ala Ala Gln Tyr Tyr Thr Tyr Lys Arg Pro Arg Gln Trp Leu Ser
465                 470                 475                 480 tcg gct ggt ctg ggc gca atg gga ttt ggg ctg cct gct gca gct ggt            1488
Ser Ala Gly Leu Gly Ala Met Gly Phe Gly Leu Pro Ala Ala Ala Gly
                485                 490                 495 gct tct gtg gct aac cca ggt gtc aca gtt gtt gat att gat ggg gat            1536
Ala Ser Val Ala Asn Pro Gly Val Thr Val Val Asp Ile Asp Gly Asp
                500                 505                 510 ggt agc ttc ctc atg aac att cag gag ctg gca ttg atc cgc att gag            1584
Gly Ser Phe Leu Met Asn Ile Gln Glu Leu Ala Leu Ile Arg Ile Glu
            515                 520                 525 aac ctc cct gtg aag gtg atg gtg ttg aac aac caa cat ttg ggt atg            1632
Asn Leu Pro Val Lys Val Met Val Leu Asn Asn Gln His Leu Gly Met
530                 535                 540 gtg gtg caa tgg gag gat agg ttt tac aag gcg aat agg gcg cat aca            1680
Val Val Gln Trp Glu Asp Arg Phe Tyr Lys Ala Asn Arg Ala His Thr
545                 550                 555                 560 tac ttg ggc aac ccg gaa tgt gag agc gag ata tat cca gat ttt gtg            1728
Tyr Leu Gly Asn Pro Glu Cys Glu Ser Glu Ile Tyr Pro Asp Phe Val
                565                 570                 575 act att gct aag ggg ttc aat att cct gca gtc cgt gta aca aag aag            1776
Thr Ile Ala Lys Gly Phe Asn Ile Pro Ala Val Arg Val Thr Lys Lys
                580                 585                 590 agt gaa gtc cgt gcc gcc atc aag aag atg ctc gag act cca ggg cca            1824
Ser Glu Val Arg Ala Ala Ile Lys Lys Met Leu Glu Thr Pro Gly Pro
            595                 600                 605 tac ttg ttg gat atc atc gtc ccg cac cag gag cat gtg ctg cct atg            1872
Tyr Leu Leu Asp Ile Ile Val Pro His Gln Glu His Val Leu Pro Met
        610                 615                 620 atc cca agt ggg ggc gca ttc aag gac atg atc ctg gat ggt gat ggc            1920
Ile Pro Ser Gly Gly Ala Phe Lys Asp Met Ile Leu Asp Gly Asp Gly
625                 630                 635                 640 agg act gtg tat taa                                                        1935
Arg Thr Val Tyr <210> SEQ ID NO 39
<211> LENGTH: 644
<212> TYPE: PRT
<213> ORGANISM: Oryza sativa

<400> SEQUENCE: 39

Met Ala Thr Thr Ala Ala Ala Ala Ala Ala Leu Ser Ala Ala Ala
1               5                   10                  15
```

```
Thr Ala Lys Thr Gly Arg Lys Asn His Gln Arg His His Val Leu Pro
         20                  25                  30

Ala Arg Gly Arg Val Gly Ala Ala Val Arg Cys Ser Ala Val Ser
         35                  40                  45

Pro Val Thr Pro Pro Ser Pro Ala Pro Ala Thr Pro Leu Arg Pro
 50                  55                  60

Trp Gly Pro Ala Glu Pro Arg Lys Gly Ala Asp Ile Leu Val Glu Ala
 65                  70                  75                  80

Leu Glu Arg Cys Gly Val Ser Asp Val Phe Ala Tyr Pro Gly Gly Ala
             85                  90                  95

Ser Met Glu Ile His Gln Ala Leu Thr Arg Ser Pro Val Ile Thr Asn
                100                 105                 110

His Leu Phe Arg His Glu Gln Gly Glu Ala Phe Ala Ala Ser Gly Tyr
             115                 120                 125

Ala Arg Ala Ser Gly Arg Val Gly Val Cys Val Ala Thr Ser Gly Pro
 130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
             165                 170                 175

Thr Asp Ala Phe Gln Glu Thr Pro Ile Val Glu Val Thr Arg Ser Ile
         180                 185                 190

Thr Lys His Asn Tyr Leu Val Leu Asp Val Glu Asp Ile Pro Arg Val
         195                 200                 205

Ile Gln Glu Ala Phe Phe Leu Ala Ser Ser Gly Arg Pro Gly Pro Val
210                 215                 220

Leu Val Asp Ile Pro Lys Asp Ile Gln Gln Met Ala Val Pro Val
225                 230                 235                 240

Trp Asp Thr Ser Met Asn Leu Pro Gly Tyr Ile Ala Arg Leu Pro Lys
             245                 250                 255

Pro Pro Ala Thr Glu Leu Leu Glu Gln Val Leu Arg Leu Val Gly Glu
         260                 265                 270

Ser Arg Arg Pro Ile Leu Tyr Val Gly Gly Gly Cys Ser Ala Ser Gly
         275                 280                 285

Asp Glu Leu Arg Trp Phe Val Glu Leu Thr Gly Ile Pro Val Thr Thr
 290                 295                 300

Thr Leu Met Gly Leu Gly Asn Phe Pro Ser Asp Asp Pro Leu Ser Leu
305                 310                 315                 320

Arg Met Leu Gly Met His Gly Thr Val Tyr Ala Asn Tyr Ala Val Asp
             325                 330                 335

Lys Ala Asp Leu Leu Leu Ala Phe Gly Val Arg Phe Asp Asp Arg Val
         340                 345                 350

Thr Gly Lys Ile Glu Ala Phe Ala Ser Arg Ala Lys Ile Val His Ile
         355                 360                 365

Asp Ile Asp Pro Ala Glu Ile Gly Lys Asn Lys Gln Pro His Val Ser
 370                 375                 380

Ile Cys Ala Asp Val Lys Leu Ala Leu Gln Gly Leu Asn Ala Leu Leu
385                 390                 395                 400

Gln Gln Ser Thr Thr Lys Thr Ser Asp Phe Ser Ala Trp His Asn
             405                 410                 415

Glu Leu Asp Gln Gln Lys Arg Glu Phe Pro Leu Gly Tyr Lys Thr Phe
         420                 425                 430

Gly Glu Glu Ile Pro Pro Gln Tyr Ala Ile Gln Val Leu Asp Glu Leu
```

-continued

```
              435                 440                 445
Thr Lys Gly Glu Ala Ile Ile Ala Thr Gly Val Gly Gln His Gln Met
    450                 455                 460

Trp Ala Ala Gln Tyr Tyr Thr Tyr Lys Arg Pro Arg Gln Trp Leu Ser
465                 470                 475                 480

Ser Ala Gly Leu Gly Ala Met Gly Phe Gly Leu Pro Ala Ala Ala Gly
                485                 490                 495

Ala Ser Val Ala Asn Pro Gly Val Thr Val Val Asp Ile Asp Gly Asp
                500                 505                 510

Gly Ser Phe Leu Met Asn Ile Gln Glu Leu Ala Leu Ile Arg Ile Glu
                515                 520                 525

Asn Leu Pro Val Lys Val Met Val Leu Asn Asn Gln His Leu Gly Met
    530                 535                 540

Val Val Gln Trp Glu Asp Arg Phe Tyr Lys Ala Asn Arg Ala His Thr
545                 550                 555                 560

Tyr Leu Gly Asn Pro Glu Cys Glu Ser Glu Ile Tyr Pro Asp Phe Val
                565                 570                 575

Thr Ile Ala Lys Gly Phe Asn Ile Pro Ala Val Arg Val Thr Lys Lys
                580                 585                 590

Ser Glu Val Arg Ala Ala Ile Lys Lys Met Leu Glu Thr Pro Gly Pro
                595                 600                 605

Tyr Leu Leu Asp Ile Ile Val Pro His Gln Glu His Val Leu Pro Met
    610                 615                 620

Ile Pro Ser Gly Gly Ala Phe Lys Asp Met Ile Leu Asp Gly Asp Gly
625                 630                 635                 640

Arg Thr Val Tyr
```

METHOD FOR TRANSFORMATION USING MUTANT ACETOLACTATE SYNTHASE GENE

This Application is the National Phase application under 35 U.S.C. § 371 of PCT International Application No. PCT/JP2006/309622 which has an International filing date of May 9, 2006, which claims priority to Japanese Application No. 2005-136186 filed on May 9, 2005.

TECHNICAL FIELD

The present invention relates to a method for transformation and a method for cultivating a plant using a mutant acetolactate synthase in which a mutation is introduced into a predetermined position of a wild-type acetolactate synthase.

BACKGROUND ART

Acetolactate synthase (hereinafter referred to as "ALS") is a rate-limiting enzyme in the biosynthetic pathway of branched chain amino acids, such as leucine, valine, and isoleucine, and is known as an essential enzyme for the growth of plants. ALS is also known to be present in a wide variety of higher plants. In addition, ALS has been discovered in various microorganisms, such as yeast (*Saccharomyces cerevisiae*), *Escherichia coli*, and *Salmonella typhimurium*.

Three types of isoenzymes of ALS are known to be present in *Escherichia coli* and *Salmonella typhimurium*. Each of these isoenzymes is a hetero oligomer consisting of catalytic subunits with large molecular weights that govern catalytic activity of the enzyme and regulatory subunits with small molecular weights that function as feedback inhibitors through binding of branched-chain amino acids (Chipman et al., Biochim. Biophys. Acta. 1385, 401-419, 1998 [Non-patent document 1]). Catalytic subunits are located at the Ilv IH, Ilv GM, and Ilv BN operons, respectively. Also, ALS in yeast is a single enzyme consisting of a catalytic subunit and a regulatory subunit, as in the case of bacteria (Pang et al., Biochemistry, 38, 5222-5231, 1999 [Non-patent document 2]). The catalytic protein subunit is located at the locus ILV2.

In plants, ALS is known to consist of catalytic subunits and regulatory subunits, as in the case of the above microorganisms (Hershey et al., Plant Molecular Biology 40, 795-806, 1999 [Non-patent document 3]). For example, the catalytic subunits of ALS in tobacco (dicotyledon) are coded by two gene loci, SuRA and SuRB (Lee et al., EMBO J. 7, 1241-1248, 1988 [Non-patent document 4]); and those in maize are coded by two gene loci, als 1 and als 2 (Burr et al., Trends in Genetics 7, 55-61, 1991 [Non-patent document 5]; Lawrence et al., Plant Mol. Biol. 18, 1185-1187, 1992 [Non-patent document 6]). The nucleotide sequences of genes coding for catalytic subunits have been completely determined for dicotyledonous plants including tobacco, *Arabidopsis*, rapeseed, cotton, *Xanthium, Amaranthus*, and Kochia (See Chipman et al., Biochim. Biophys. Acta. 1385, 401-419, 1998 [Non-patent document 1] and International Publication WO97/08327 [Patent document 1]). However, maize and rice are the only monocotyledonous plants for which nucleotide sequences have been completely determined.

Meanwhile, herbicides, such as sulfonylurea herbicides, imidazolinon herbicides, triazolopyrimidine herbicides, and pyrimidinyl carboxy herbicides (hereinafter referred to as "PC herbicides"), are known to suppress plant growth by inhibiting ALS (Ray, Plant Physiol. 75, 827-831, 1984 [Non-patent document 7]; Shaner et al., Plant Physiol. 76, 545-546, 1984 [Non-patent document 8]; Subramanian et al., Plant Physiol. 96, 310-313, 1991 [Non-patent document 9]; and Shimizu et al., J. Pestic. Sci. 19, 59-67, 1994 [Non-patent document 10].

Plants with one or two nucleotide substitutions in a gene coding for ALS, which induce one or two amino acid substitutions in a region conserved among different species, are known as plants having resistance to these herbicides. Examples of such a gene include a gene coding for ALS having strong resistance to sulfonylurea herbicides (see Kathleen et al., EMBO J. 7, 1241-1248, 1988 [Non-patent document 11]; Mourad et al., Planta, 188, 491-497, 1992 [Non-patent document 12]; Guttieri et al., Weed Sci. 43, 175-178, 1995 [Non-patent document 13]; Bernasconi et al., J. Biol. Chem. 270, 17381-17385, 1995 [Non-patent document 14]; and JP Patent Publication (Kokai) No. 63-71184 A (1988) [Patent document 2]); a gene coding for ALS having strong resistance to imidazolinon herbicides (see Mourad et al., Planta, 188, 491-497, 1992 [Non-patent document 12]; Lee et al., FEBS Lett. 452, 341-345, 1999 [Non-patent document 15], and JP Patent Publication (Kokai) No. 5-227964 A (1993) [Patent document 3]); a gene coding for ALS having strong resistance to PC herbicides (see WO02/44385A1 [Patent document 4] and WO03/083118A1 [Patent document 5]); and a gene coding for ALS having resistance to sulfonylurea, imidazolinon, and PC herbicides (see Kathleen et al., EMBO J. 7, 1241-1248, 1988 [Non-patent document 11]; Bernasconi et al., J. Biol. Chem. 270, 17381-17385, 1995 [Non-patent document 14]; Hattori et al., Mol. Gen. Genet. 246, 419-425, 1995 [Non-patent document 16]; Alison et al., Plant Physiol. 111, 1353, 1996 [Non-patent document 17]; Rajasekarau et al., Plant Sci. 119, 115-124, 1996 [Non-patent document 18]; JP Patent Publication (Kokai) No. 63-71184 A (1988) [Patent document 2]; JP Patent Publication (Kokai) No. 4-311392 A (1992) [Patent document 6]; Bernasconi et al., U.S. Pat. No. 5,633,437, 1997 [Patent document 7]; WO02/44385A1 [Patent document 4]; and WO03/083118A1 [Patent document 5]).

The production of a plant that exerts resistance to both sulfonylurea and imidazolinon herbicides has been attempted by crossing a plant having ALS that exerts resistance specifically to sulfonylurea herbicides with a plant having ALS that exerts resistance specifically to imidazolinon herbicides (Mourad et al., Mol. Gen. Genet, 243, 178-184, 1994 [Non-patent document 19]). Furthermore, artificial alteration of a gene coding for ALS into a herbicide resistance gene has been attempted (see Ott et al., J. Mol. Biol. 263, 359-368, 1996 [Non-patent document 20]; JP Patent Publication (Kokai) No. 63-71184 A (1988) [Patent document 2]; JP Patent Publication (Kokai) No. 5-227964 A (1993) [Patent document 3]; and JP Patent Publication (Kohyo) No. 11-504213 A (1999) [Patent document 8]). It has thus been revealed that a single amino acid deletion causes ALS to exert resistance to both sulfonylurea and imidazolinon herbicides (see JP Patent Publication (Kokai) No. 5-227964 A (1993) [Patent document 3]).

As described above, ALSs having resistance to herbicides and genes coding for ALSs have been aggressively studied. However, no cases have been reported to date concerning a mutant ALS gene having resistance specifically to PC herbicides alone using resistance to PC herbicides as an indicator. If a mutant ALS gene having specific resistance to a specific herbicide is obtained, such mutant ALS gene can be used for various applications. No cases have been reported to date concerning such mutant ALS gene, which is useful in terms of specificity to PC herbicides.

Non-patent document 1 Chipman et al., Biochim. Biophys. Acta. 1385, 401-419, 1998

Non-patent document 2 Pang et al., Biochemistry, 38, 5222-5231, 1999

Non-patent document 3 Hershey et al., Plant Molecular Biology 40, 795-806, 1999

Non-patent document 4 Lee et al., EMBO J. 7, 1241-1248, 1988

Non-patent document 5 Burr et al., Trends in Genetics 7, 55-61, 1991

Non-patent document 6 Lawrence et al., Plant Mol. Biol. 18, 1185-1187, 1992

Non-patent document 7 Ray, Plant Physiol. 75, 827-831, 1984

Non-patent document 8 Shaner et al., Plant Physiol. 76, 545-546, 1984

Non-patent document 9 Subramanian et al., Plant Physiol. 96, 310-313, 1991

Non-patent document 10 Shimizu et al., J. Pestic. Sci. 19, 59-67, 1994

Non-patent document 11 Kathleen et al., EMBO J. 7, 1241-1248, 1988

Non-patent document 12 Mourad et al., Planta, 188, 491-497, 1992

Non-patent document 13 Guttieri et al., Weed Sci. 43, 175-178, 1995

Non-patent document 14 Bernasconi et al., J. Biol. Chem. 270, 17381-17385, 1995

Non-patent document 15 Lee et al., FEBS Lett. 452, 341-345, 1999

Non-patent document 16 Hattori et al., Mol. Gen. Genet. 246, 419-425, 1995

Non-patent document 17 Alison et al., Plant Physiol. 111, 1353, 1996

Non-patent document 18 Rajasekarau et al., Plant Sci. 119, 115-124, 1996

Non-patent document 19 Mourad et al., Mol. Gen. Genet, 243, 178-184, 1994

Non-patent document 20 Ott et al., J. Mol. Biol. 263, 359-368, 1996

Patent document 1 International Publication WO97/08327

Patent document 2 JP Patent Publication (Kokai) No. 63-71184 A (1988)

Patent document 3 JP Patent Publication (Kokai) No. 5-227964 A (1993)

Patent document 4 International Publication WO02/44385

Patent document 5 International Publication WO03/083118

Patent document 6 JP Patent Publication (Kokai) No. 4-311392 A (1992)

Patent document 7 Bernasconi et al., U.S. Pat. No. 5,633,437

Patent document 8 JP Patent Publication (Kohyo) No. 11-504213 A (1999)

DISCLOSURE OF THE INVENTION

Under the above-described circumstances, an object of the present invention is to provide a method for efficiently selecting a transformed cell with the use of a mutant ALS gene having high specificity to PC herbicides.

As a result of intensive studies to achieve the above object, we have revealed that ALS having a specific mutation exerts extremely high resistance to PC herbicides. We have also discovered that a gene coding for ALS having such mutation can be used as a selection marker. Therefore, we have completed the present invention.

The present invention encompasses the following.

(1) A transformation method, comprising the steps of:
transforming a host cell with a recombination vector containing a gene of interest and a gene coding for a mutant acetolactate synthase having mutation of glycine corresponding to position 95 of the amino acid sequence of a wild-type acetolactate synthase derived from rice to alanine; and
culturing the transformed cell obtained in the former step in the presence of a pyrimidinyl carboxy herbicide,
wherein the gene coding for the mutant acetolactate synthase is used as a selection marker.

(2) The transformation method according to (1), wherein the gene coding for the mutant acetolactate synthase is a gene coding for the following protein (a) or (b):
(a) a protein comprising the amino acid sequence of SEQ ID NO: 2; or
(b) a protein comprising an amino acid sequence derived from the amino acid sequence of SEQ ID NO: 2 by substitution, deletion, or addition of at least one amino acid other than alanine of position 95, having resistance to a pyrimidinyl carboxy herbicide, and having acetolactate synthase activity.

(3) The transformation method according to (1), wherein the host cell is a plant cell.

(4) A method for cultivating a plant, comprising the steps of:
transforming a plant cell with a recombination vector containing a gene of interest and a gene coding for a mutant acetolactate synthase having mutation of glycine corresponds to position 95 of the amino acid sequence of a wild-type acetolactate synthase derived from rice to alanine; and
cultivating the transformed plant obtained in the former step in the presence of a pyrimidinyl carboxy herbicide,
wherein the gene coding for the mutant acetolactate synthase is used as a selection marker.

(5) The method for cultivating a plant according to (4), wherein the gene coding for the mutant acetolactate synthase is a gene coding for the following protein (a) or (b):
(a) a protein comprising the amino acid sequence of SEQ ID NO: 2; or
(b) a protein comprising an amino acid sequence derived from the amino acid sequence of SEQ ID NO: 2 by substitution, deletion, or addition of at least one amino acid other than alanine of position 95, having resistance to a pyrimidinyl carboxy herbicide, and having acetolactate synthase activity.

This description includes part or all of the contents disclosed in the description and/or drawings of Japanese Patent Application No. 2005-136186, which is priority document of the present application.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 1 shows an amino acid sequence comparison between a mutant ALS protein derived from rice and a wild-type ALS protein (SEQ ID NO: 39) derived from rice.

FIG. 2-1 shows a nucleotide sequence comparison between a mutant ALS gene derived from rice and a gene (SEQ ID NO: 38) coding for a wild-type ALS protein derived from rice.

FIG. 2-2 shows a nucleotide sequence comparison between a mutant ALS gene derived from rice and a gene (SEQ II) NO: 38) coding for a wild-type ALS protein derived from rice.

FIG. 2-3 shows a nucleotide sequence comparison between a mutant ALS gene derived from rice and a gene (SEQ ID NO: 38) coding for a wild-type ALS protein derived from rice.

FIG. 3 shows photographs showing the rooting of clones derived from the G95A-1 line and the G95A-2 line in rooting medium containing bispyribac-sodium as observed.

FIG. 4 is a schematic diagram for explaining a method for constructing a G95A mutant ALS expression vector (SEQ ID NO: 24).

BEST MODE FOR CARRYING OUT THE INVENTION

Figure 5:
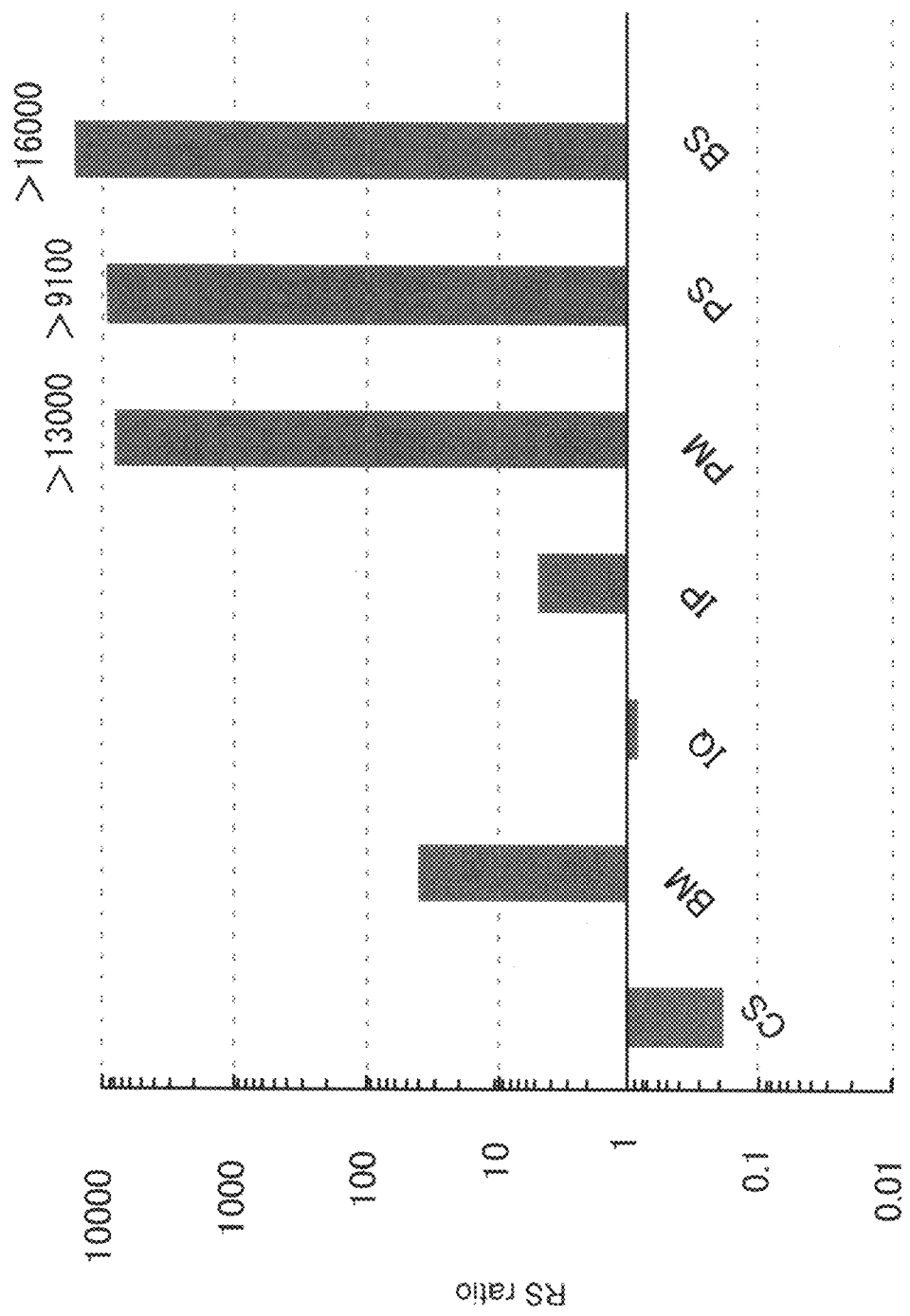
FIG. 5 is a characteristic figure showing the herbicide resistance ratio (RS ratio) of G95A mutant ALS to wild-type ALS based on 50% inhibitory concentration.

Hereunder, a more detailed explanation of the present invention will be given.

The acetolactate synthase protein of the present invention (hereinafter referred to as "mutant ALS protein") can be obtained through mutation of a predetermined site in a wild-type ALS protein. In a wild-type ALS protein derived from rice, the $95^{th}$ amino acid from N-terminal methionine is glycine. In the mutant ALS protein of the present invention, glycine 95 has been substituted with alanine. Specifically, such mutant ALS protein derived from rice according to the present invention has an amino acid sequence in which glycine 95 has been substituted with alanine (denoted as G95A). The nucleotide sequence of a gene (hereinafter, referred to as a "mutant ALS gene") coding for such mutant ALS protein derived from rice and the amino acid sequence of such mutant ALS protein are shown in SEQ ID NOS: 1 and 2, respectively.

FIG. 1 shows an amino acid sequence comparison between the mutant ALS protein derived from rice and the wild-type ALS protein derived from rice. Further, in FIG. 1, the amino acid sequence in the $1^{st}$ row represents the wild-type ALS protein and the amino acid sequence in the $2^{nd}$ row represents the mutant ALS protein.

Unlike the gene coding for the wild-type ALS protein derived from rice, the mutant ALS gene (SEQ ID NO: 1) derived from rice is obtained through substitution of codons coding for glycine 95 in the wild-type ALS protein with codons coding for alanine. FIGS. 2-1 to 2-3 show a nucleotide sequence comparison between the mutant ALS gene derived from rice and the gene coding for the wild-type ALS protein derived from rice. In addition, in FIGS. 2-1 to 2-3, the nucleotide sequence in the $1^{st}$ row represents the mutant ALS gene and the nucleotide sequence in the $2^{nd}$ row represents the gene coding for the wild-type ALS protein.

Such mutant ALS gene can be obtained by introducing the above-described mutation into a gene coding for a wild-type ALS protein that is present in the genomic DNA of Taichung 65 (japonica type rice variety). Any conventionally known techniques can be employed as techniques for introducing mutations. For example, site-directed mutagenesis can be employed. Site-directed mutagenesis can be performed using a commercial kit, e.g., Mutan-K (Takara Shuzo), Gene Editor (Promega), or ExSite (Stratagene). In addition, a gene coding for the mutant ALS protein can be obtained by culturing wild-type cells sensitive to a PC herbicide in the presence of the PC herbicide and then obtaining the gene from mutant cells that appear and exert resistance to the PC herbicide.

The mutant ALS gene according to the present invention can be obtained not only from the gene derived from rice shown in SEQ ID NO: 1, but also from ALS genes derived from a wide variety of plants. For example, the mutant ALS gene according to the present invention can be obtained by introducing a similar mutation into an ALS gene derived from maize, wheat, barley, soybean, cotton, rapeseed, sugar beet, Italian ryegrass, tobacco, *Arabidopsis thaliana*, or the like.

Here, "similar mutation" means a mutation of glycine corresponding to glycine of position 95 (this number may differ depending on the plants in question) in a wild-type ALS protein derived from rice to alanine.

The amino acid sequences of two types of mutant ALS protein derived from maize are shown in SEQ ID NOS: 3 and 4, respectively. Partial amino acid sequences of two types of mutant ALS protein derived from wheat are shown in SEQ ID NOS: 5 and 6, respectively. The amino acid sequences of two types of mutant ALS protein derived from cotton are shown in SEQ ID NOS: 7 and 8, respectively. The amino acid sequences of two types of mutant ALS protein derived from rapeseed are shown in SEQ ID NOS: 9 and 10, respectively. The amino acid sequences of two types of mutant ALS protein derived from tobacco are shown in SEQ ID NOS: 11 and 12, respectively. The amino acid sequence of a mutant ALS protein derived from Italian ryegrass is shown in SEQ ID NO: 13. The amino acid sequence of a mutant ALS protein derived from *Arabidopsis thaliana* is shown in SEQ ID NO: 14.

The mutant ALS protein according to the present invention exerts resistance specifically to PC herbicides regardless of its origin, as long as glycine corresponding to glycine 95 of a wild-type ALS protein derived from rice has been substituted with alanine.

Compared with wild-type ALS proteins, the mutant ALS protein shows high resistance to PC herbicides. This can be confirmed by incorporating a gene coding for the mutant ALS protein into an expression vector in *Escherichia coli*, for example, and then examining the sensitivity of the mutant ALS (obtained from the thus transformed *Escherichia coli* using the expression vector) to PC herbicides.

Here, examples of PC herbicides include bispyribac-sodium, pyrithiobac-sodium, and pyriminobac, as represented by the following chemical formulas 1.

Formulas 1:

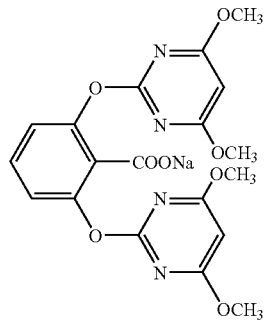

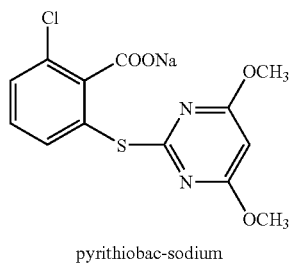

pyrithiobac-sodium

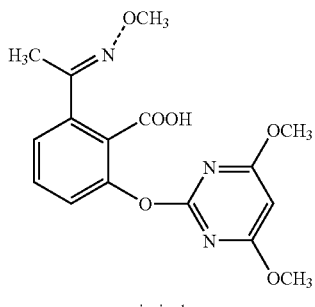

pyriminabac

The expression "... exerts resistance specifically to PC herbicides" means that resistance to sulfonylurea herbicides or imidazolinon herbicides other than PC herbicides is significantly lower than resistance to PC herbicides. Examples of such sulfonylurea herbicides include, as represented by chemical formulas 2, chlorsulfuron, bensulfuron-methyl, pyrazosulfuron-ethyl, and imazosulfuron.

Formulas 2:

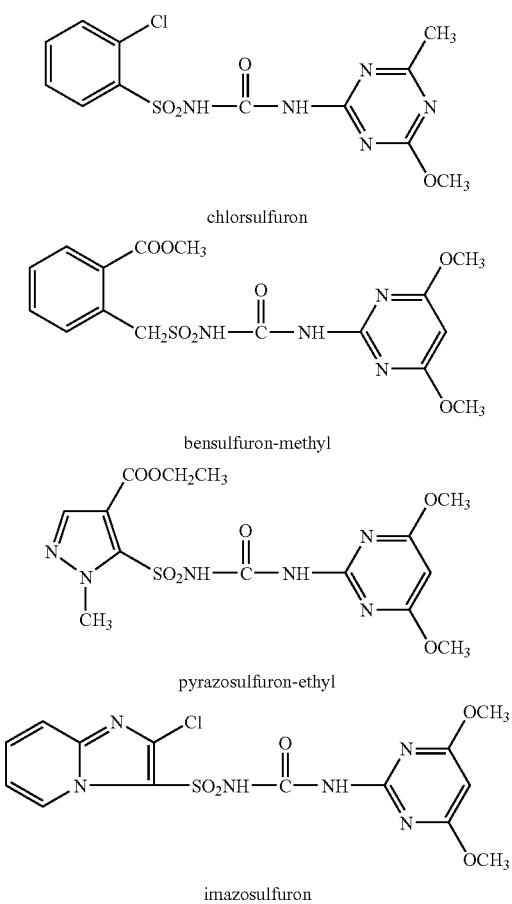

Examples of imidazolinone herbicides include imazaquin and imazapyr, as represented by the following chemical formulas 3.

Formulas 3:

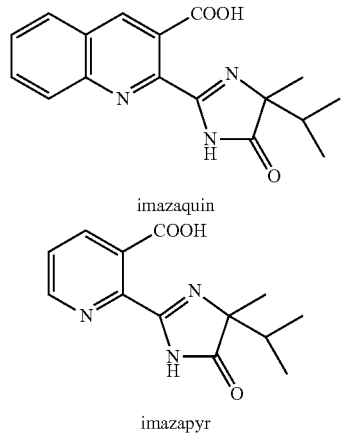

According to the present invention, a transformation method can be constructed that enables efficient transformation with a gene of interest through the use of a mutant ALS gene. Specifically, such mutant ALS gene can be used as a selection marker in an experiment for plant transformation. For example, to transform a plant cell using a gene of interest, a recombination vector having the mutant ALS gene and a gene of interest is introduced into the plant cell and then the plant cell is cultured in the presence of a PC herbicide. If the thus obtained plant cells survive in the presence of the PC herbicide, they are confirmed to be plant cells into which the gene of interest has been introduced together with the mutant ALS gene. Further, whether the gene of interest and the gene coding for the mutant ALS protein have been incorporated into the chromosomes of the plant cells can be confirmed by observing the phenotype of the plants and then examining the presence of these genes on the genome, by genome southern hybridization or PCR.

As techniques for transformation of plants, conventionally known techniques can be employed. An example of such a technique is a technique that involves introducing a foreign gene into a target plant cell using *Agrobacterium* (*Agrobacterium tumefaciens*).

More specifically, the mutant ALS gene and a gene of interest are inserted into a binary vector containing the T-DNA sequence of a Ti plasmid of *Agrobacterium*. The Ti plasmid is transformed into *Escherichia coli* or the like. Then, the binary vectors retaining the mutant ALS gene and the gene of interest replicated by, e.g., *Escherichia coli* are transformed into *Agrobacterium* sp. that contain helper plasmids. Target plants are infected with the *Agrobacterium* sp. and then the transformed plants are identified. When the identified transformed plants are in the form of culture cells, the plant cells can be regenerated into complete plants by a conventionally known technique.

To transform a target plant with such recombination vector having the mutant ALS gene and a gene of interest, the vector may be directly introduced into the plant using a conventionally known technique. Furthermore, examples of a method for transformation with such recombination vector having the mutant ALS gene and a gene of interest include a polyethylene glycol method, an electroporation method, a particle gun method and the like.

Meanwhile, the mutant ALS gene and a gene of interest may be transformed into any types of plants, such as monocotyledonous and dicotyledonous plants. Examples of a target crop to be transformed with such a gene coding for the mutant ALS protein include rice, maize, wheat, barley, soybean, cotton, rapeseed, sugar beet, tobacco and the like. In addition, turf grass, trees, and the like can also be transformed through introduction of such mutant gene and a gene of interest.

In any of the above cases, transformation of a plant using a mutant ALS gene can impart resistance specifically to PC herbicides to the plant. In particular, PC herbicides are water soluble, unlike sulfonylurea herbicides or imidazolinone herbicides, so that they are easy to handle. Furthermore, the use of such a PC herbicide makes it possible to eliminate the effects of an organic solvent on host cells. Therefore, such a PC herbicide is preferably used as a herbicide upon transformation. Moreover, such a PC herbicide exerts activity to inhibit ALS that is approximately 100 times greater than that of an imidazolinone herbicide. Thus, transformants can be selected using an extremely small amount of the PC herbicide.

The present invention will be further described by the following examples, but the technical scope of the invention is not limited by these examples.

Example 1

Callus (Derived from Anther Culture) Induction

Young panicles having an auricle-to-auricle length ranging from 6 cm to 8 cm were collected, so that the maximum number of anthers at the mononuclear phase could be obtained from "Taichung 65 (a japonica rice cultivar)" in the booting stage. At such time, portions of the stems below the nodes of the prophylls of cotyledons were cut n water. Leaves other than two leaf types (a cotyledon and a prophyll thereof), which directly enwrap each young panicle, were removed.

The base portions of the stems were wrapped with paper towels soaked with water and then covered with vinyl bags, so that low temperature treatment was performed for 5 to 10 days under dark conditions at 10° C. Subsequently, the young panicles were removed within a clean bench, sterilized with 70% ethanol for 10 minutes, and then dried on sterilized kimtowels (Crecia, Tokyo). Semitransparent glumaceous flowers containing anthers at the mononuclear phase were opened using sterilized tweezers. Only the anthers were removed and then placed on callus induction medium (N6CI medium, Table 1). The anthers were cultured under continuous light conditions at 30° C. They were subcultured on new medium every 3 weeks.

TABLE 1

| Callus induction medium (N6CI), pH 5.8 | |
|---|---|
| N6 inorganic salt | |
| N6 vitamin | |
| Sucrose | 30 g/l |
| 2.4-D | 2 mg/l |
| L(−)-proline | 2.878 g/l |
| Gelrite | 3 g/l |
| Casamino acids | 0.3 g/l |

Example 2

Selection of Callus (Derived from Anther Culture) Using Bispyribac-Sodium

Calli (derived from anther culture) in 5 weeks after callus induction were cultured on callus induction medium containing 0.25 µM bispyribac-sodium for 4 weeks. Next, the grown calli were cultured on redifferentiation medium (Table 2) containing 0.5 µM bispyribac-sodium for 4 weeks. Thus, redifferentiated albino plants were obtained. Subculture was performed every 2 weeks in all cases.

TABLE 2

| Redifferentiated medium (pH 5.8) | |
|---|---|
| MS inorganic salt | |
| N6 vitamin | |
| Sucrose | 30 g/l |
| Sorbitol | 50 g/l |
| 2.4-D | 2 mg/l |
| NAA | 1 mg/l |
| BAP | 2 mg/l |
| Casamino acids | 2 g/l |
| L(−)-proline | 2.878 g/l |
| Gelrite | 4 g/l |

The medium was adjusted to have a total volume of 1 liter, autoclaved, and then supplemented with bispyribac-sodium.

Example 3

Bispyribac-Sodium Resistance Test

The two lines of plants selected by the above method were designated the G95A-1 line and the G95A-2 line. Since they were albino plants, they were cultured on MS medium and then multiplied by division. To test the degree of resistance to bispyribac-sodium, clone plants divided from the G95A-1 line were transplanted on rooting media (Table 3) containing 0 µM, 1 µM, 5 µM, 10 µM, or 20 µM bispyribac-sodium (FIG. 3A: on the left in each Petri dish, observed as white because they were albino). Clone plants of the G95A-2 line (the number of these clone plants is a few) were tested using 5 µM bispyribac-sodium alone. Plants of wild-type Taichung 65 in 2 weeks after seeding were used as members of a control group (FIG. 3, on the right side in each Petri dish). Plant in 1 week (FIG. 3B) after transplantation and plant in 2 weeks (FIG. 3C) after transplantation were observed. As a result, the plants of both the G95A-1 and the G95A-2 lines exerted resistance, with new rooting observed for both thereof at all bispyribac-sodium-containing medium concentrations. However, all the wild-type plants of the control group withered on bispyribac-sodium-containing media.

TABLE 3

| Rooting test medium (pH 5.8) | |
|---|---|
| MS inorganic salt | |
| N6 vitamin | |
| Sucrose | 30 g/l |
| Agar | 8 g/l |

The medium was adjusted to have a total volume of 1 liter, autoclaved, and then supplemented with bispyribac-sodium.

Example 4

Analysis of ALS Gene Sequences of Bispyribac-Sodium-Resistant Albino Lines

Leaves (approximately 0.5×1 cm) of the two above lines were placed in 1.5 ml tubes and then dried at 50° C. for 2 or more hours. Four glass beads BZ-3 (Iuchiseieido) with a diameter of 3 mm each were placed within each tube. Leaves were pulverized using a mixer mill MM300 (Retsch). After pulverization, 300 μl of an extraction buffer (200 mM Tris-HCl (pH. 7.5), 250 mM NaCl, 25 mM EDTA, and 0.5% SDS) was added, so that the pulverized product was suspended. The suspension was centrifuged at 14,000 rpm for 5 minutes. 200 μl of the supernatant was transferred into a new tube and then 200 μl of isopropanol was added. The resultant was centrifuged at 14,000 rpm for 5 minutes, the supernatant was removed, and then the thus obtained precipitate was vacuum-dried for 3 minutes. 50 μl of ⅕×TE was added to the precipitate. The resultant was centrifuged at 14,000 rpm for 1 minute, and thus a genomic DNA solution was prepared.

The sequences of all the regions of ALS genes were analyzed by PCR direct sequencing using the thus prepared genomic DNA as a template and the following primers. ExTaq (TAKARA BIO INC.) was used for PCR. After initial denaturation at 94° C. for 1 minute, 40 cycles of reaction were performed, each consisting of 94° C. for 30 seconds, 58° C. for 30 seconds, and 72° C. for 40 seconds. With a combination of ALSF2 and ALS2R primers, PCRx enhancer (Invitrogen) was added, initial denaturation was performed at 94° C. for 1 minute, and then 40 cycles of reaction were performed, each consisting of 94° C. for 1 minute, 50° C. for 1 minute, and 72° C. for 1 minute. Each PCR product was subjected to agarose electrophoresis and then purified using a Mini Elute Gel Extraction kit (QIAGEN).

Sequencing reactions were performed using the PCR products as templates, an ABI Sequencing kit, and the following primers. When ALSF2 and ALS2R primers were used, a Sequence Rx enhancer solution A (Invitrogen) was added. 35 cycles of sequencing reaction were performed under conditions of 96° C. for 10 seconds, 50° C. for 5 seconds, and 60° C. for 4 minutes. After sequencing reaction, nucleotide sequences were determined using an ABI PRISM 310 Genetic Analyzer (Applied Biosystems, U.S.A.).

ALSF2 (5'-CCACCACCCACCATGGCTACG-3', sense primer corresponding to nucleotides—12 to 9 of ALS gene, and SEQ ID NO: 15)

ALS2R (5'-GAAGAGGTGGTTGGTGATGA-3', antisense primer corresponding to nucleotides 326 to 345 of ALS gene, and SEQ ID NO: 16)

ALS12 (5'-GCAACCAACCTCGTGTCCGC-3, sense primer corresponding to nucleotides 436 to 455 of ALS gene, and SEQ ID NO: 17)

ALS22 (5'-GAAGGCTTCCTGTATGACGC-3', antisense primer corresponding to nucleotides 620 to 639 of ALS gene, and SEQ ID NO: 18)

ALS13 (5'-GAATTGCGCTGGTTTGTTGA-3', sense primer corresponding to nucleotides 868 to 887 of ALS gene, and SEQ ID NO: 19)

ALS23 (5'-CTCAATTTTCCCTGTCACACG-3', antisense primer corresponding to nucleotides 1051 to 1071 of ALS gene, and SEQ ID NO: 20)

ALS24F (5'-GGTAGCTTCCTCATGAACAT-3', sense primer corresponding to nucleotides 1537 to 1556 of ALS gene, and SEQ ID NO: 21)

ALS24R (5'-AATGTTCATGAGGAAGCTAC-3', antisense primer corresponding to nucleotides 1538 to 1557 of ALS gene, and SEQ ID NO: 22)

ALS25 (5'-CATTCAGGTCAAACATAGGCC-3', antisense primer corresponding to nucleotides 1919 to 1989 of ALS gene, and SEQ ID NO: 23)

The ALS gene sequences of the above two lines were examined as described above. In both lines, amino acid 95 (glycine (GGC)) of ALS had been substituted with alanine (GCC) through single-nucleotide substitution.

Example 5

Construction of Vector for Expression of GST-Fusion G95A Mutant ALS

Amplification was performed using W548L/S627I double-point mutant ALS (see WO02/44385A1) derived from rice incorporated in a pUC18 vector as a template, a sense primer ALS-M5 (5'-TACCCGGGCNNNGCGTCCATG-GAGATCCA-3': corresponding to amino acids 92 to 101 of the amino acid sequence of SEQ ID NO: 24) prepared via degeneration of codons corresponding to glycine 95, and an antisense primer ALS-RspA (5'-TGTGCTTGGTGATGGA-3'; SEQ ID NO: 25) corresponding to amino acid 191 to 196 of the amino acid sequence. The thus amplified PCR product was cloned into a pT7Blue-T vector. *Escherichia coli* (HB-101 strain) was transformed with the vector according to a conventional method.

With the same primer set, colony PCR and sequence analysis were performed. Thus, colonies in which glycine (GGC) 95 had been mutated to serine (AGC), cysteine (TGC), tyrosine (TAT), alanine (GCA), valine (GTG), leucine (CTG), isoleucine (ATA), methionine (ATG), tryptophan (TGG), phenylalanine (TTT), aspartic acid (GAT), glutamic acid (GAG), or arginine (CGG) were obtained. In the case of the alanine mutant, the plasmid was extracted after liquid culture of *Escherichia coli* and then digested with Sma I. After electrophoresis, a mutant ALS gene fragment was purified from the agarose gel. The gene fragment was ligated to a pUC18 vector in which W548L/S627I double-point mutant ALS gene derived from rice (that had been digested with Sma I and then treated with BAP for purification) had been incorporated. A Nco I fragment containing a G95A portion was excised from the thus obtained pUC18 vector containing a G95A/W548L/S627I three-point mutant ALS gene. The excised Nco I fragment was ligated to a protein expression vector (pGEX-2T) for *Escherichia coli* in which a wild-type ALS gene (that had been treated with Nco I and then treated with BAP) had been incorporated. Therefore, a pGEX-2T expression vector containing a G95A single-point mutant ALS gene was obtained (FIG. 4).

Example 6

Confirmation of the Nucleotide Sequence of the pGEX-2T Vector in which the G95A Mutant ALS Gene was Incorporated The *Escherichia coli* (JM109 strain) transformed with the vector was cultured in ten tubes (2 ml, respectively) at 37° C. for 12 hours. The plasmid (500 μl) was extracted using a plasmid extraction apparatus (TOMY DP-480) and concentrated by centrifugation to approximately 200 μl. The product was desalted using a GFX PCR and Gel Purification Kit (Amersham Bioscience) and then finally eluted with 200 μl of sterilized water. The plasmid was subjected to a sequencing reaction using a BigDye Terminator ver.1.1 cycle sequencing kit (Applied Biosystems).

[Total volume: 20 μl (template DNA 13 μl, primer (3.2 pmol/μl) 1 μl, pre-mix 4 μl, and dilution buffer 2 μl), reaction conditions: initial denaturing at 96° C. (5 minutes) and 40 cycles each consisting of denaturing at 96° C. (5 seconds), annealing at 50° C. (5 seconds), and elongation at 60° C. (4 minutes), followed by elongation in the final cycle at 60° C. (9 minutes)]

After the sequencing reaction, fluorescent nucleotides in the reaction solution were removed by gel filtration using an AutoSeq G-50 column (Amersham Bioscience). The reaction sample was measured using an ABI PRIZM 310 genetic analyzer and then the sequence was confirmed. The following primer sequences were used as primers for sequencing.

PGEX-5 (5'-GGGCTGGCAAGCCACGTTTGGTG-3', sense primer, on the upstream side of ALS gene, and SEQ ID NO: 26)

ALS-RspC (5'-CAGCGACGTGTTCGCCTA-3', sense primer corresponding to nucleotides 258 to 275 of ALS gene, and SEQ ID NO: 27)

ALS-M1 (5'-CCCCAGCCGCATGATCGGCACCGACGC-CTT-3', sense primer corresponding to nucleotides 510 to 539 of ALS gene, and SEQ ID NO: 28)

ALS-Rsp3 (5'-CTGGGACACCTCGATGAAT-3', sense primer corresponding to nucleotides 720 to 738 of ALS gene, and SEQ ID NO: 29)

ALS-Rsp7 (5'-AACTGGGATACCAGTCAGCTC-3', antisense primer corresponding to nucleotides 886 to 906 of ALS gene, and SEQ ID NO: 30)

ALS-Rsp1 (5'-GCTCTGCTACAACAGAGCACA-3', sense primer corresponding to nucleotides 1192 to 1212 of ALS gene, and SEQ ID NO: 31)

3-1-3 (5'-GATTGCCTCACCTTTCG-3', antisense primer corresponding to nucleotides 1346 to 1362 of ALS gene, and SEQ ID NO: 32)

4-83-10 (5'-CAGCCCAAATCCCATTG-3', antisense primer corresponding to nucleotides 1457 to 1473 of ALS gene, and SEQ ID NO: 33)

3-1-4 (5'-AGGTGTCACAGTTGTTG-3', sense primer corresponding to nucleotides 1506 to 1522 of ALS gene, and SEQ ID NO: 34)

ALS-RspB (5'-TCAAGGACATGATCCTGGATGG-3', sense primer corresponding to nucleotides 1892 to 1913 of ALS gene, and SEQ ID NO: 35)

ALS-Rsp2 (5'-AGTCCTGCCATCACCATCCAG-3', antisense primer corresponding to nucleotides 1906 to 1926 of ALS gene, and SEQ ID NO: 36)

PGEX-3 (5'-CCGGGAGCTGCATGTGTCAGAGG-3', antisense primer, on the downstream side of ALS gene, and SEQ ID NO: 37)

Example 7

Expression of G95A Mutant ALS and Preparation of ALS

The *Escherichia coli* transformed with pGEX-2T having a G95A mutant ALS gene prepared in Example 6 and the same transformed with pGEX-2T (see WO02/44385A1) having a wild-type ALS gene were each shake-cultured (preculture) in 2 ml of LB liquid medium containing ampicillin at 27° C. They were each cultured in 250 ml of LB liquid medium containing ampicillin using 1 ml of the preculture solution. After overnight culture, 1 mM IPTG was added and they were further cultured for 3 to 4 hours. Thus, the expression of the GST fusion protein was induced. In addition, microbial bodies were washed with an ALS extraction buffer (potassium phosphate buffer (pH 7.5) containing 30% glycerol and 0.5 mM MgCl$_2$) and then stored at −80° C.

Preparation and purification of ALS from *Escherichia coli* were performed by the following method. First, a pellet of the *Escherichia coli* stored at −80° C. was suspended in an ALS extraction buffer. (2.5 ml of the ALS extraction buffer was added to the pellet obtained from 50 ml of the culture solution.) The suspension was subjected to ultrasonication (Heat Systems-Ultrasonics, Sonicator W-225R, micro chip, output control 8, intervals of approximately 1 second, and twice every 40 seconds), and then centrifuged at 15000×g and 4° C. for 20 minutes, thereby obtaining the supernatant as a crude enzyme solution. Therefore, a crude enzyme solution of the GST fusion G95A mutant ALS protein and a crude enzyme solution of the GST fusion wild-type ALS protein were prepared.

Example 8

Determination of the Activity of Expressed ALS

A reaction solution to be used for the reaction for activity determination was prepared by mixing GST fusion ALS to be subjected to activity determination with a solution comprising 20 mM sodium pyruvate, 0.5 mM thiamine pyrophosphate, 0.5 mM MgCl$_2$, 10 µM flavin adenine dinucleotide, 10 mM valine (added for the inhibition of activity of ALS derived from *Escherichia coli*), and 20 mM potassium phosphate buffer (pH 7.5). 0.5 ml of the reaction solution was used. The reaction was performed at 37° C. for 30 minutes after addition of GST fusion ALS to be subjected to activity determination. The reaction was stopped by the addition of 0.05 ml of 6 N sulfuric acid. After the completion of the reaction, the reaction solution was subjected to incubation at 37° C. for 60 minutes, so that acetolactic acid contained in the reaction solution was converted into acetoin. Subsequently, to quantify acetoin contained in the reaction solution, 0.05 ml of 0.5% (w/v) creatine and 0.05 ml of 5% (w/v) α-naphthol dissolved in 2.5 N sodium hydroxide were added, followed by 10 minutes of incubation at 37° C. Acetoin was then quantified by color comparison of the absorbance at 525 nm of the reaction solution, thereby evaluating ALS activity. The value at reaction time 0 (hours) was used as a control value. When the herbicide inhibition activity was examined, aqueous solutions of bispyribac-sodium and pyrithiobac-sodium were each prepared at a 100-fold concentration and then added to the reaction solution. In the case of pyriminobac, chlorsulfuron, bensulfuron-methyl, imazaquin, and imazapyr having low water solubility, an acetone solution was prepared for each thereof at a 100-fold concentrations and then added to the reaction solution.

Example 9

Sensitivity of G95A Mutant ALS Against Herbicides

The inhibition activity of various ALS inhibitors against the thus expressed G95A mutant ALS was examined. It was thus revealed that the inhibition activity of bispyribac-sodium, that of pyrithiobac-sodium, and that of pyriminobac were extremely weak (50% or less inhibition activity at 100 µM), but the inhibition activity of chlorsulfuron was strong, and bensulfuron-methyl, imazaquin, and imazapyr also exerted inhibition activity (Table 4).

TABLE 4

| Sensitivity of G95A mutant ALS against herbicides | | | | | | |
|---|---|---|---|---|---|---|
| BS | PS | PM | CS | BM | IQ | IP |
| First | 17.9% | 12.1% | 22.9% | 0.0023 | 0.268 | 1.653 | 46.041 |
| Second | 16.8% | 12.8% | 23.3% | 0.0030 | 0.294 | 1.886 | 44.612 |
| Third | 18.4% | 18.1% | 29.2% | 0.0027 | 0.271 | 1.848 | 49.705 |
| Fourth | — | — | — | 0.0028 | — | — | — |
| Fifth | — | — | — | 0.0021 | — | — | — |
| Sixth | — | — | — | 0.0019 | — | — | — |

TABLE 4-continued

Sensitivity of G95A mutant ALS against herbicides

|  | BS | PS | PM | CS | BM | IQ | IP |
|---|---|---|---|---|---|---|---|
| Average | 17.7% | 14.3% | 25.1% | 0.0025 | 0.278 | 1.80 | 46.8 |
| SE | 0.47% | 1.9% | 2.0% | 0.0002 | 0.008 | 0.07 | 1.52 |

BS: bispyribac-sodium,
PS: pyrithiobac-sodium,
PM: pyriminobac
CS: chlorsulfuron,
BM: bensulfuron-methyl,
IQ: imazaquin,
IP: imazapyr In addition, in Table 4, the unit for all numerical figures where no unit is indicated is µM (50% inhibitory concentration). Numerical figures indicated with "%" denote inhibition % at 100 µM. SE denotes standard error.

The 50% inhibitory concentration of each herbicide against G95A mutant ALS was compared with the 50% inhibitory concentration of the herbicide against wild-type ALS (GST fusion wild-type ALS), so that the herbicide resistance ratio (RS ratio) of the 50% inhibitory concentration against G95A mutant ALS to that against wild-type ALS was calculated. The RS ratios in the cases of bispyribac-sodium, pyrithiobac-sodium, and pyriminobac were 16,000:1 or more, 9,100:1 or more, and 13,000:1 or more, respectively. In contrast, the RS ratios in the cases of chlorsulfuron, bensulfuron-methyl, imazaquin, and imazapyr were 0.19:1, 40:1, 0.82:1, and 4.9:1, respectively. Hence, it was demonstrated that G95A mutant ALS specifically exerts strong resistance to PC herbicides (Table 5 and FIG. 5). Furthermore, in FIG. 5, BS denotes bispyribac-sodium, PS denotes pyrithiobac-sodium, PM denotes pyriminobac, CS denotes chlorsulfuron, BM denotes bensulfuron-methyl, IQ denotes imazaquin, and IP denotes imazapyr.

TABLE 5

Ratio of resistance against herbicides; G95A mutant ALS to wild type

| | 50% inhibitory concentration (µM) | | Resistance ratio |
|---|---|---|---|
| Herbicide | Wild type | G95A mutant | (RS ratio) |
| Bispyribac-sodium | 0.0063 | >100 | >16000 |
| Pyrithiobac-sodium | 0.011 | >100 | >9100 |
| Pyriminobac | 0.0080 | >100 | >13000 |
| Chlorsulfuron | 0.013 | 0.0025 | 0.19 |
| Bensulfuron-methyl | 0.0070 | 0.28 | 40 |
| Imazaquin | 2.2 | 1.8 | 0.82 |
| Imazapyr | 9.6 | 47 | 4.9 |

CONCLUSION

According to the above Examples, it was revealed that the mutant ALS protein prepared by introducing a G95A mutation into the wild-type ALS protein derived from rice exerts resistance specifically to pyrimidinyl carboxy herbicides. It was thus demonstrated that through the use of the properties of the mutant ALS protein exerting such excellent specificity, cells expressing the mutant ALS protein can be efficiently selected with certainty from cells not expressing such protein in the presence of PC herbicides.

Furthermore, an ALS gene derived from rice was used in the above Examples. However, the technical scope of the present invention is not limited to the transformation method using the mutant ALS gene derived from rice. In general, it is known that ALS genes share high homology across different plants. Moreover, it is also known that a specific mutation in an ALS gene has similar effects on a plural number of plant species. Therefore, according to the Examples, it was revealed that mutant ALS proteins derived from maize, wheat, barley, soybean, cotton, rapeseed, sugar beet, tobacco, and the like having a mutation that was the same as that of the G95A mutation similarly exert resistance specifically to pyrimidinyl carboxy herbicides.

INDUSTRIAL APPLICABILITY

As described in detail above, according to the present invention, a transformation method can be provided that is excellent in efficiency through the use of a mutant acetolactate synthase that exerts extremely high resistance to PC herbicides as a selection marker.

All publications, patents, and patent applications cited herein are incorporated herein by reference in their entirety.

The invention claimed is:

1. A transformation method for increasing specific resistance to a pyrimidinyl carboxy herbicide, comprising the steps of:
    transforming a host cell with a recombination vector containing a gene of interest and a gene coding for a mutant acetolactate synthase where alanine is in place of glycine at the position corresponding to position 95 of the amino acid sequence of a wild-type acetolactate synthase derived from rice (SEQ ID NO: 39);
    culturing the transformed cell obtained in the former step in the presence of a pyrimidinyl carboxy herbicide, and
    wherein the gene coding for the mutant acetolactate synthase is used as a selection marker.

2. The transformation method according to claim 1, wherein the mutant acetolactate synthase comprises at least one of the amino acid sequences selected from the group consisting of SEQ ID NOs: 2-14.

3. The transformation method according to claim 1, wherein the host cell is a plant cell.

4. A method for cultivating a plant having specific resistance to a pyrimidinyl carboxy herbicide, comprising the steps of:
    transforming a plant cell with a recombination vector containing a gene of interest and a gene coding for a mutant acetolactate synthase where alanine is in place of glycine at the position corresponding to position 95 of the amino acid sequence of a wild-type acetolactate synthase derived from rice (SEQ ID NO: 39);
    cultivating the transformed plant cell obtained in the former step in the presence of a pyrimidinyl carboxy herbicide, and wherein the gene coding for the mutant acetolactate synthase is used as a selection marker.

5. The method for cultivating a plant according to claim 4, wherein the mutant acetolactate synthase comprises at least one of the amino acid sequences selected from the group consisting of SEQ ID NOs: 2-14.

6. The transformation method of claim 1, wherein said culturing step is performed in the presence of a pyrimidinyl carboxy herbicide and in the absence of an sulfonyl urea herbicide.

* * * * *